(12) United States Patent
Sakuma et al.

(10) Patent No.: US 8,404,726 B2
(45) Date of Patent: Mar. 26, 2013

(54) ACTIVATING AGENT FOR PEROXISOME PROLIFERATOR ACTIVATED RECEPTOR δ

(75) Inventors: Shogo Sakuma, Saitama (JP); Nobutaka Mochiduki, Chiba (JP); Rie Takahashi, Saitama (JP); Masatoshi Ushioda, Tokyo (JP); Tomio Yamakawa, Chiba (JP); Seiichiro Masui, Saitama (JP)

(73) Assignee: Nippon Chemiphar Co. Ltd., Tokyo (JP)

( * ) Notice: Subject to any disclaimer, the term of this patent is extended or adjusted under 35 U.S.C. 154(b) by 318 days.

(21) Appl. No.: 12/297,436

(22) PCT Filed: Apr. 18, 2007

(86) PCT No.: PCT/JP2007/058899
§ 371 (c)(1),
(2), (4) Date: Feb. 17, 2009

(87) PCT Pub. No.: WO2007/119887
PCT Pub. Date: Oct. 25, 2007

(65) Prior Publication Data
US 2009/0298896 A1    Dec. 3, 2009

(30) Foreign Application Priority Data
Apr. 18, 2006  (JP) ............................. 2006-114561

(51) Int. Cl.
*A61K 31/426* (2006.01)
*C07D 277/30* (2006.01)
*A61P 3/00* (2006.01)
*A61P 9/10* (2006.01)

(52) U.S. Cl. ........ 514/365; 548/204; 548/217; 548/233; 514/340; 514/314; 514/326

(58) Field of Classification Search ............... None
See application file for complete search history.

(56) References Cited

U.S. PATENT DOCUMENTS

| | | |
|---|---|---|
| 4,956,379 A | 9/1990 | Meanwell |
| 5,089,514 A | 2/1992 | Hulin |
| 5,723,479 A | 3/1998 | Sohda et al. |
| 6,043,264 A | 3/2000 | Ohtake et al. |
| 6,300,364 B1 | 10/2001 | Shimokawa et al. |
| 6,589,969 B1 | 7/2003 | Tajima et al. |
| 6,787,552 B2 | 9/2004 | Sakuma et al. |
| 7,078,422 B2 | 7/2006 | Sakuma et al. |
| 7,119,104 B2 | 10/2006 | Sakuma et al. |
| 7,265,137 B2 | 9/2007 | Sakuma et al. |
| 2002/0032330 A1 | 3/2002 | Nomura et al. |
| 2003/0109570 A1 | 6/2003 | Tsunoda et al. |
| 2003/0171377 A1* | 9/2003 | Bigge et al. .............. 514/254.03 |
| 2005/0054674 A1* | 3/2005 | Sakuma et al. ............... 514/314 |
| 2005/0080115 A1 | 4/2005 | Jeppesen et al. |
| 2005/0107449 A1* | 5/2005 | Conner et al. .................. 514/365 |
| 2007/0155805 A1 | 7/2007 | Harling et al. |
| 2008/0194564 A1 | 8/2008 | Zeiller et al. |

FOREIGN PATENT DOCUMENTS

| | | |
|---|---|---|
| CA | 2457054 | 2/2003 |
| EP | 505322 | 9/1992 |
| EP | 558062 | 9/1993 |
| EP | 1310494 A1 | 2/2002 |
| EP | 1184366 | 6/2002 |
| JP | 2003-292439 | 10/2003 |
| WO | WO 92/10468 | 6/1992 |
| WO | WO 96/20935 | 7/1996 |
| WO | WO 96/35688 | 11/1996 |
| WO | WO 97/27190 | 7/1997 |
| WO | WO 97/28115 | 8/1997 |
| WO | WO 01/00603 * | 1/2001 |
| WO | WO 01/16120 | 3/2001 |
| WO | WO 01/40207 | 6/2001 |
| WO | WO 01/79197 | 10/2001 |
| WO | WO 02/50048 | 6/2002 |
| WO | WO 02/059098 | 8/2002 |
| WO | WO 02/067912 | 9/2002 |
| WO | WO 02/092590 | 11/2002 |
| WO | 03018553 | 3/2003 |

(Continued)

OTHER PUBLICATIONS

Sznaidman et al. In Bioorganic and Medicinal Chemistry Letters vol. 13, pp. 1517-1521 (2003).*
Patani et al. In Chemical Reviews 1996, 96, 3147-3176.*
Sznaidman et al. In Bioorganic and Medicinal Chemistry Letters 13 (2003) 1517-1521.*
Oliver et al. In Proceedings of the National Academy of Sciences U.S.A 98, 5306-5311 (2001).*
Akiyama e al, In Current Diabetes Reports 2005, 5:45-52).*
Kliewer et al., *Nature* 358:771-774 (1992).
Kliewer et al., *Proc Natl Acad Sci USA* 91:7355-7359 (1994).
Kuwabaka et al., *J Pharmacol Exp Ther* 309(3):970, 2004.
Pilli et al., *Archiv der Pharmazie* 326(9):559-561, 1993.
Sznaidman et al. *Bioorg Med Chem Lett* 13:1517-1521, 2003.
Berger, J. et al., 1999, *J Biol Chem* 274:6718-6725.
Bright, S. et al., 1997, *J Immunol Methods* 207(1):23-31.
He, T.-C. et al., 1999, *Cell* 99:335-345.
Isseman, I. et al., 1990, *Nature* 347:645-650.

(Continued)

*Primary Examiner* — Dennis Heyer
(74) *Attorney, Agent, or Firm* — Jones Day

(57) ABSTRACT

A compound represented by the following general formula (II) or a salt thereof is used as an activator of PPARδ.

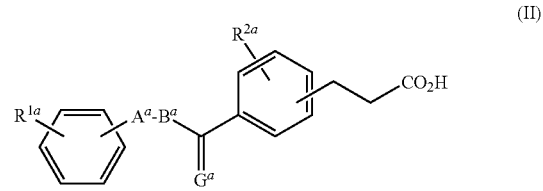

(II)

wherein $G^a$ is O, $CH_2$ or the like;
$A^a$ is thiazole, oxazole, or thiophene, which can have a substituent such as $C_{1-8}$ alkyl, $C_{1-8}$ alkoxy, halogen, $C_{1-8}$ alkyl substituted with halogen or the like;
$B^a$ is a $C_{1-8}$ alkylene or $C_{2-8}$ alkenylene chain; and
each of $R^{1a}$ and $R^{2a}$ independently is hydrogen, $C_{1-8}$ alkyl, $C_{1-8}$ alkoxy, halogen, $C_{1-8}$ alkyl substituted with halogen or the like.

3 Claims, No Drawings

FOREIGN PATENT DOCUMENTS

| | | |
|---|---|---|
| WO | WO 03/099793 | 12/2003 |
| WO | WO 2004/007439 | 1/2004 |
| WO | WO 2004/018475 | 3/2004 |
| WO | WO 2004/022551 | 3/2004 |
| WO | WO 2004/063166 | 7/2004 |
| WO | WO 2004/063184 | 7/2004 |
| WO | WO 2004/063190 | 7/2004 |
| WO | WO 2004/071509 | 8/2004 |
| WO | WO 2005/049578 | 6/2005 |
| WO | WO 2005/054213 | 6/2005 |
| WO | WO 2005/077926 | 8/2005 |
| WO | WO 2005/115384 | 12/2005 |
| WO | WO 2006/125324 | 11/2006 |
| WO | WO 2007/004733 | 1/2007 |
| WO | WO 2007/119887 | 10/2007 |
| WO | WO 2008/016175 | 2/2008 |

OTHER PUBLICATIONS

Kidwai et al., *Acta Pharmaceutica* (Zagreb), 47(1):53-57 (1997).
Lehmann, J. et al., 1997, *J Biol Chem* 272(6):3406-3410.
Mano H., et al., 2000, *J Biol Chem* 175:8126-8132.
Oliver, W. et al., 2001, *Proc Natl Acad Sci USA* 98(9):5306-5311.
Uhle & Harris, *J Am Chem Society* 79:102-109 (1957).
Office Action dated Nov. 3, 2006 for U.S. Appl. No. 10/486,783.
Office Action dated Apr. 3, 2007 for U.S. Appl. No. 11/544,505.
Office Action dated Sep. 17, 2007 for U.S. Appl. No. 11/544,505.
Advisory Action dated Jan. 4, 2008 for U.S. Appl. No. 11/544,505.
Office Action dated May 20, 2011 for U.S. Appl. No. 12/297,436.
Office Action dated Jan. 10, 2012 for U.S. Appl. No. 12/297,436.
Advisory Action dated May 16, 2012 for U.S. Appl. No. 12/297,436.
Office Action dated Feb. 4, 2009 for U.S. Appl. No. 11/888,492.
Office Action dated Mar. 25, 2009 for U.S. Appl. No. 11/888,493.

* cited by examiner

ACTIVATING AGENT FOR PEROXISOME PROLIFERATOR ACTIVATED RECEPTOR δ

RELATED APPLICATIONS

This application claims the benefit of Japanese Application No. 2006-114561, filed on Apr. 18, 2006, the content of which is hereby incorporated by reference in its entirety.

TECHNICAL FIELD

The present invention relates to an activator of peroxisome proliferator activated receptor (PPAR).

PRIOR ART

As the activator of peroxisome proliferator activated receptor (PPAR), three subtypes, namely PPARα, PPARγ and PPARδ have been identified (Proc. Natl. Acad. Sci. USA, 91, p7335-7359, 1994).

Various compounds have been reported with respect to functions of activating transcription of the PPAR subtypes, lowering blood sugar level, or improving metabolism of lipid. For example, GW-590735 (GSK), KRP-101 (Kyorin) and NS-220 (Roche-Nippon Shinyaku) have been reported as a selective α-agonist having the function of improving metabolism of lipid (J Pharmacol Exp Ther 309(3): 970, June 2001).

Other agents have a function as a dual agonist for PPARγ and PPARα. For example, TZD (thiazolidinedione) derivatives such as KRP-297 (Kyorin) and others such as Muraglitazar (BMS) and Tesaglitazar (AstraZeneca), which are shown below, have been known as the agents have the function. The compounds have been developed as agents for treatment of diabetes to have a main function for PPARα. Therefore, it is reported that the compounds do not have a strong function for PPARγ.

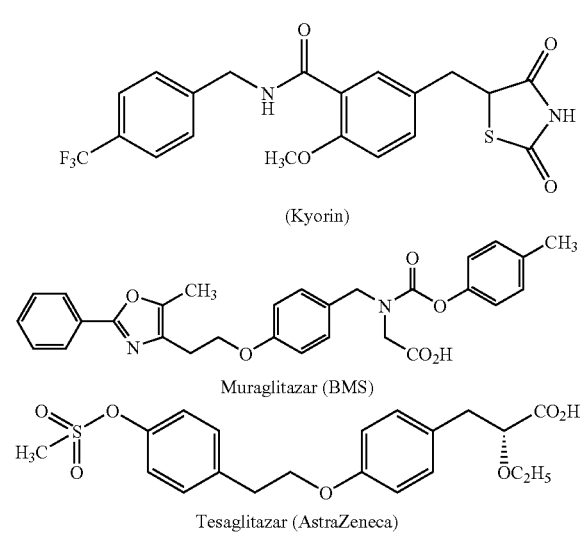

As a selective agonist for PPARδ, GW-501516 (GSK) having the following formula of phenoxyacetic acid type has been known. WO 01/603 and Bioorg Med Chem Lett 13 (2003) 1517-1521 report that the compound has been developed as an agent for improving metabolism of lipid.

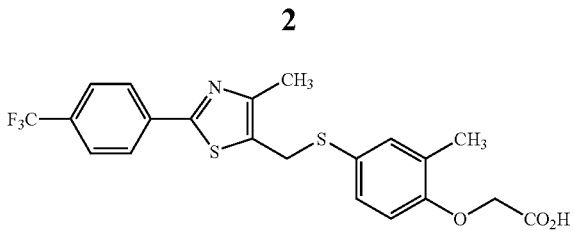

WO 01/603 further discloses the following compounds of phenylglycine type and phenylpropionic acid type.

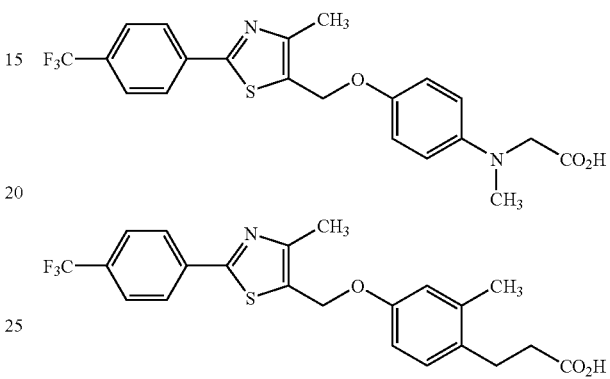

The present inventors have filed WO 02/76957, which describes that the following compound of phenylacetic acid type has a function of activating transcription of PPARδ.

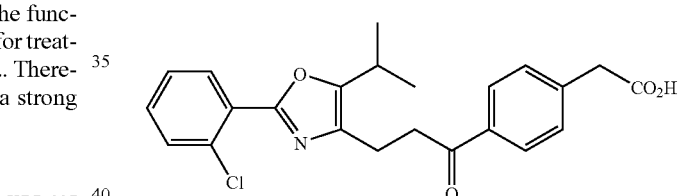

The present inventors have further filed WO 03/16291, which describes that a compound of substituted phenoxyacetic acid type also has an excellent function of activating transcription of PPARδ.

WO 04/63184 has recently discloses a compound of phenylpropionic acid type having thiophene in its formula as a PPAR modulator.

Bioorg Med Chem Lett 13 (2003) 1517-1521 describes that the activating function of phenylpropionic acid type for PPARδ is about 30 times weaker than the function of phenoxyacetic acid type.

WO 01/603 and Bioorg Med Chem Lett 13 (2003) 1517-1521 are silent with respect to a metical effect of the phenylglycine type.

The compounds represented by the formula (I), (II) and (III) according to the present invention differ from the above-mentioned compounds such as GW-501516. The above-mentioned documents are silent with respect to the compounds.

DISCLOSURE OF INVENTION

An object of the invention is to provide compounds represented by the formula (I), (II) and (III), which have a function of activating peroxisome proliferator activated receptor.

The present inventors have studied and discovered that compounds of phenylpropionic acid type unexpectedly has an excellent function of activating peroxisome proliferator activated receptor δ, which is different from the descriptions in Bioorg Med Chem Lett 13 (2003) 1517-1521. The present invention has been completed based on the discovery.

The present invention resides in a compound having the following formula (I) or a salt thereof:

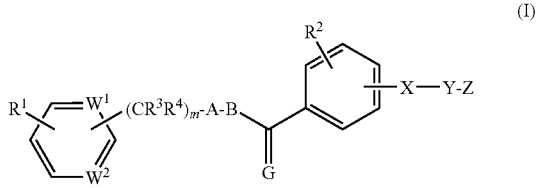

wherein each of $W^1$ and $W^2$ independently is CH or nitrogen;

X is $NR^5$ or $CR^6R^7$, wherein $R^5$ is hydrogen, $C_{1-8}$ alkyl, $C_{1-8}$ alkyl substituted with halogen, $C_{1-8}$ alkyl substituted with $C_{1-8}$ alkoxy, cycloalkyl of three-membered to seven-membered ring, $C_{1-8}$ alkyl substituted with cycloalkyl of three-membered to seven-membered ring, $C_{1-8}$ alkyl substituted with phenyl, $C_{2-8}$ acyl, or $C_{2-8}$ alkenyl, and each of $R^6$ and $R^7$ independently is hydrogen or $C_{1-8}$ alkyl;

Y is $—(CR^8R^9)_n—$, wherein each of $R^8$ and $R^9$ independently is hydrogen or $C_{1-8}$ alkyl, and n is 1 to 4; or X and Y are combined to form $—CR^{10}=CR^{11}—$ or ethynylene, wherein each of $R^{10}$ and $R^{11}$ independently is hydrogen or $C_{1-8}$ alkyl;

Z is carboxyl or tetrazolyl;

G is O, S or $CR^{12}R^{13}$, wherein each of $R^{12}$ and $R^{13}$ independently is hydrogen or $C_{1-8}$ alkyl;

A is five-membered heterocyclic ring selected from the group consisting of thiazole, oxazole, imidazole, pyrazole, thiophene, furan, and pyrrole, which can be substituted with a substituent selected from the group consisting of $C_{1-8}$ alkyl, $C_{2-8}$ alkenyl, $C_{2-8}$ alkynyl, $C_{1-8}$ alkoxy, halogen, $C_{1-8}$ alkyl substituted with halogen, $C_{1-8}$ alkoxy substituted with halogen, hydroxyl, nitro, $C_{2-8}$ acyl, $C_{6-10}$ aryl, and a five-membered or six-membered heterocyclic group;

B is a $C_{1-8}$ alkylene, $C_{2-8}$ alkenylene or $C_{2-8}$ alkynylene chain, wherein the chain can be substituted with a substituent selected from the group consisting of $C_{1-8}$ alkyl, cycloalkyl of three-membered to seven-membered ring, $C_{1-8}$ alkoxy, and halogen;

each of $R^1$ and $R^2$ independently is hydrogen, $C_{1-8}$ alkyl, $C_{2-8}$ alkenyl, $C_{2-8}$ alkynyl, $C_{1-8}$ alkoxy, halogen, $C_{1-8}$ alkyl substituted with halogen, $C_{1-8}$ alkoxy substituted with halogen, hydroxyl, nitro, $C_{2-8}$ acyl, $C_{6-10}$ aryl, or a five-membered or six-membered heterocyclic group;

each of $R^3$ and $R^4$ independently is hydrogen or $C_{1-8}$ alkyl; and m is an integer of 0 to 3.

The invention also resides in a compound having the following formula (II) or a salt thereof:

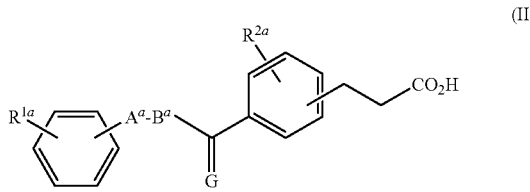

wherein $G^a$ is O, S or $CH_2$;

$A^a$ is five-membered heterocyclic ring selected from the group consisting of thiazole, oxazole, and thiophene, which can be substituted with a substituent selected from the group consisting of $C_{1-8}$ alkyl, $C_{1-8}$ alkoxy, halogen, $C_{1-8}$ alkyl substituted with halogen, $C_{1-8}$ alkoxy substituted with halogen, hydroxyl, nitro, and $C_{2-8}$ acyl;

$B^a$ is a $C_{1-8}$ alkylene or $C_{2-8}$ alkenylene chain; and each of $R^{1a}$ and $R^{2a}$ independently is hydrogen, $C_{1-8}$ alkyl, $C_{1-8}$ alkoxy, halogen, $C_{1-8}$ alkyl substituted with halogen, $C_{1-8}$ alkoxy substituted with halogen, hydroxyl, nitro, or $C_{2-8}$ acyl.

The invention further resides in a compound having the following formula (III) or a salt thereof:

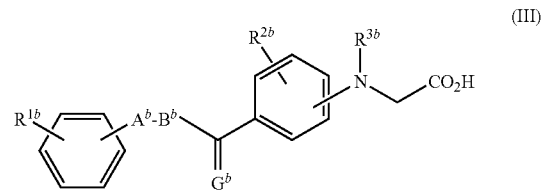

wherein $G^b$ is O, S or $CH_2$;

$A^b$ is five-membered heterocyclic ring selected from the group consisting of thiazole, oxazole, and thiophene, which can be substituted with a substituent selected from the group consisting of $C_{1-8}$ alkyl, $C_{1-8}$ alkoxy, halogen, $C_{1-8}$ alkyl substituted with halogen, $C_{1-8}$ alkoxy substituted with halogen, hydroxyl, nitro, and $C_{2-8}$ acyl;

$B^b$ is a $C_{1-8}$ alkylene or $C_{2-8}$ alkenylene chain;

each of $R^{1b}$ and $R^{2b}$ independently is hydrogen, $C_{1-8}$ alkyl, $C_{1-8}$ alkoxy, halogen, $C_{1-8}$ alkyl substituted with halogen, $C_{1-8}$ alkoxy substituted with halogen, hydroxyl, nitro, or $C_{2-8}$ acyl; and $R^{3b}$ is hydrogen or $C_{1-8}$ alkyl.

The present invention relates to an activator of peroxisome proliferator activated receptor δ which contains as an effective component a compound having the formula (I), (II), or (III) or a salt thereof.

The invention also relates to a method of activating peroxisome proliferator activated receptor δ, characterized in that effective dose of a compound having the formula (I), (II), or (III) or a salt thereof is administered as an effective component.

The invention further relates to a method for treatment and/or prophylaxis of a disease mediated by peroxisome proliferator activated receptor δ, such as dyslipidemia, metabolic syndrome, obesity including internal organs fat type, atherosclerosis or disease associated therewith, or diabetes, characterized in that effective dose of a compound having the formula (I), (II), or (III) or a salt thereof is administered as an effective component.

The invention furthermore relates to use of a compound having the formula (I), (II), or (III) or a salt thereof for treatment and/or prophylaxis of a disease mediated by peroxisome proliferator activated receptor δ, such as dyslipidemia, metabolic syndrome, obesity including internal-organs fat type, atherosclerosis or disease associated therewith, or diabetes.

BEST EMBODIMENTS OF INVENTION

The present invention is described below in more detail.

In the formula (I), $R^1$, $R^2$, $R^3$, $R^4$, $R^5$, $R^6$, $R^7$, $R^8$, $R^9$, $R^{10}$, $R^{11}$, $R^{12}$, $R^{13}$, a substituent of the five-membered heterocyclic ring represented by A, and a substituent of the $C_{1-8}$ alkylene, $C_{2-8}$ alkenylene or $C_{2-8}$ alkynylene chain represented by B can be $C_{1-8}$ alkyl. Examples of the $C_{1-8}$ alkyl include methyl, ethyl, propyl, isopropyl, butyl, isobutyl, t-butyl, pentyl and hexyl.

$R^1$, $R^2$, $R^5$, and a substituent of the five-membered heterocyclic ring represented by A can be $C_{2-8}$ alkenyl. Examples of the $C_{2-8}$ alkenyl include vinyl and allyl.

$R^1$, $R^2$, and a substituent of the five-membered heterocyclic ring represented by A can be $C_{2-8}$ alkynyl. Examples of the $C_{2-8}$ alkynyl include propargyl.

$R^1$, $R^2$, a substituent of the five-membered heterocyclic ring represented by A, and a substituent of the $C_{1-8}$ alkylene, $C_{2-8}$ alkenylene or $C_{2-8}$ alkynylene chain represented by B can be $C_{1-8}$ alkoxy. Examples of the $C_{1-8}$ alkoxy include methoxy, ethoxy, propoxy, isopropoxy, butoxy, isobutoxy, t-butoxy, pentyloxy, and hexyloxy.

$R^1$, $R^2$, a substituent of the five-membered heterocyclic ring represented by A, and a substituent of the $C_{1-8}$ alkylene, $C_{2-8}$ alkenylene or $C_{2-8}$ alkynylene chain represented by B can be halogen. Examples of the halogen include fluorine, chlorine, and bromine.

$R^1$, $R^2$, $R^5$, and a substituent of the five-membered heterocyclic ring represented by A can be $C_{1-8}$ alkyl substituted with halogen. Examples of the $C_{1-8}$ alkyl substituted with halogen include methyl, ethyl, propyl, isopropyl, butyl, and t-butyl which are substituted with 1-3 halogens such as fluorine, chlorine, and bromine. Preferred are trifluoromethyl, chloromethyl, 2-chloroethyl, 2-bromoethyl, and 2-fluoroethyl.

$R^1$, $R^2$, and a substituent of the five-membered heterocyclic ring represented by A can be $C_{1-8}$ alkoxy substituted with halogen. Examples of the $C_{1-8}$ alkoxy substituted with halogen include methoxy, ethoxy, propoxy, iso-propoxy, butoxy, and t-butoxy which are substituted with 1-3 halogen atoms such as fluorine atom, chlorine atom, or bromine atom. Preferred are trifluoromethoxy, chloro-methoxy, 2-chloroethoxy, 2-bromoethoxy, and 2-fluoroethoxy.

$R^1$, $R^2$, $R^5$, and a substituent of the five-membered heterocyclic ring represented by A can be $C_{2-8}$ acyl. Examples of the $C_{2-8}$ acyl include acetyl and propionyl.

$R^1$, $R^2$, and a substituent of the five-membered heterocyclic ring represented by A can be $C_{6-10}$ aryl. Examples of the $C_{6-10}$ aryl include phenyl.

$R^1$, $R^2$, and a substituent of the five-membered heterocyclic ring represented by A can be a five-membered or six-membered heterocyclic group. Examples of the five-membered or six-membered heterocyclic group include pyridyl.

$R^5$ can be $C_{1-8}$ alkyl substituted with $C_{1-8}$ alkoxy. Examples of the $C_{1-8}$ alkyl substituted with $C_{1-8}$ alkoxy include methyl, ethyl, propyl, isopropyl, butyl, isobutyl, t-butyl, pentyl and hexyl which are substituted with methoxy, ethoxy, propoxy, isopropoxy, butoxy, isobutoxy, t-butoxy, pentyloxy, or hexyloxy.

$R^5$ can be cycloalkyl of three-membered to seven-membered ring. Examples of the cycloalkyl of three-membered to seven-membered ring include cyclopropyl, cyclobutyl, cyclopentyl, and cyclohexyl.

$R^5$ can be $C_{1-8}$ alkyl substituted with cycloalkyl of three-membered to seven-membered ring. Examples of the $C_{1-8}$ alkyl substituted with cycloalkyl of three-membered to seven-membered ring include methyl, ethyl, propyl, isopropyl, butyl, isobutyl, t-butyl, pentyl and hexyl which are substituted with cyclopropyl, cyclobutyl, cyclopentyl, or cyclohexyl.

$R^5$ can be $C_{1-8}$ alkyl substituted with phenyl. Examples of the $C_{1-8}$ alkyl substituted with phenyl include benzyl and phenethyl.

A substituent of the $C_{1-8}$ alkylene, $C_{2-8}$ alkenylene or $C_{2-8}$ alkynylene chain represented by B can be cycloalkyl of three-membered to seven-membered ring. Examples of the cycloalkyl of three-membered to seven-membered ring include cyclopropyl, cyclobutyl, cyclopentyl, and cyclohexyl.

In the formula (II), $R^{1a}$, $R^{2a}$, and a substituent of five-membered heterocyclic ring represented by $A^a$ can be $C_{1-8}$ alkyl, $C_{1-8}$ alkoxy, halogen, $C_{1-8}$ alkyl substituted with halogen, $C_{1-8}$ alkoxy substituted with halogen, and $C_{2-8}$ acyl. Examples of them are the same as the examples of $R^1$, $R^2$, and the substituent of the five-membered heterocyclic ring represented by A in the formula (I).

In the formula (III), $R^{1b}$, $R^{2b}$, and a substituent of five-membered heterocyclic ring represented by $A^b$ can be $C_{1-8}$ alkyl, $C_{1-8}$ alkoxy, halogen, $C_{1-8}$ alkyl substituted with halogen, $C_{1-8}$ alkoxy substituted with halogen, and $C_{2-8}$ acyl. Examples of them are the same as the examples of $R^1$, $R^2$, and the substituent of the five-membered heterocyclic ring represented by A in the formula (I).

In the formula (III), $R^{3b}$ can be $C_{1-8}$ alkyl. Examples are the same as the examples of $R^5$ in the formula (I).

Each of $R^1$, $R^2$ in the formula (I), $R^{1a}$, $R^{2a}$ in the formula (II), $R^{1b}$ and $R^{2b}$ in the formula (III) can be one to three groups attached to the rings, such as benzene ring. The two or three groups can be different from each other.

Preferred compounds of the present invention are shown below.

(1) A compound having the formula (I) or a salt thereof, wherein each of $W^1$ and $W^2$ is CH (2) A compound having the formula (I), a salt thereof, a compound defined in (1), or a salt thereof, wherein X is $CR^6R^7$ (3) A compound having the formula (I), a salt thereof, a compound defined in (1), or a salt thereof, wherein X is $CH_2$ (4) A compound having the formula (I), a salt thereof, a compound defined in (1), or a salt thereof, wherein X is $NR^5$ (5) A compound having the formula (I), a salt thereof, a compound defined in (1), or a salt thereof, wherein X is NH (6) A compound having the formula (I), a salt thereof, a compound defined in (1), or a salt thereof, wherein X is $NR^5$, and $R^5$ is $C_{1-8}$ alkyl (7) A compound having the formula (I), a salt thereof, a compound defined in one of (1) to (6), or a salt thereof, wherein Y is $CH_2$ (8) A compound having the formula (I), a salt thereof, a compound defined in one of (1) to (7), or a salt thereof, wherein Z is carboxyl (9) A compound having the formula (I), a salt thereof, a compound defined in one of (1) to (8), or a salt thereof, wherein G is 0

(10) A compound having the formula (I), a salt thereof, a compound defined in one of (1) to (9), or a salt thereof, wherein A is thiazole, which can be substituted with a substituent selected from the group consisting of $C_{1-8}$ alkyl, $C_{2-8}$ alkenyl, $C_{2-8}$ alkynyl, $C_{1-8}$ alkoxy, halogen, $C_{1-8}$ alkyl substituted with halogen, $C_{1-8}$ alkoxy substituted with halogen, hydroxyl, nitro, $C_{2-8}$ acyl, $C_{6-10}$ aryl, and a five-membered or six-membered heterocyclic group

(11) A compound having the formula (I), a salt thereof, a compound defined in one of (1) to (10), or a salt thereof, wherein B is ethylene chain

(12) A compound having the formula (I), a salt thereof, a compound defined in one of (1) to (11), or a salt thereof, wherein each of $R^1$ and $R^2$ independently is hydrogen, $C_{1-8}$ alkyl, $C_{2-8}$ alkenyl, $C_{1-8}$ alkoxy, halogen, $C_{1-8}$ alkyl substituted with halogen, or $C_{1-8}$ alkoxy substituted with halogen

(13) A compound having the formula (I), a salt thereof, a compound defined in one of (1) to (11), or a salt thereof, wherein each of $R^1$ and $R^2$ independently is hydrogen, $C_{1-8}$ alkyl, halogen, or $C_{1-8}$ alkyl substituted with halogen

(14) A compound having the formula (I), a salt thereof, a compound defined in one of (1) to (13), or a salt thereof, wherein each of $R^3$ and $R^4$ is hydrogen

(15) A compound having the formula (I), a salt thereof, a compound defined in one of (1) to (14), or a salt thereof, wherein m is 0

(16) A compound having the formula (II) or a salt thereof, wherein $G^a$ is O.

(17) A compound having the formula (II), a salt thereof, a compound defined in (16), or a salt thereof, wherein $A^a$ is thiazole, which can be substituted with a substituent selected from the group consisting of $C_{1-8}$ alkyl, $C_{1-8}$ alkoxy, halogen, $C_{1-8}$ alkyl substituted with halogen, $C_{1-8}$ alkoxy substituted with halogen, hydroxyl, nitro, and $C_{2-8}$ acyl.

(18) A compound having the formula (II), a salt thereof, a compound defined in (16) or (17), or a salt thereof, wherein $B^a$ is ethylene chain.

(19) A compound having the formula (II), a salt thereof, a compound defined in one of (16) to (18), or a salt thereof, wherein each of $R^{1a}$ and $R^{2a}$ independently is hydrogen, $C_{1-8}$ alkyl, $C_{1-8}$ alkoxy, halogen, $C_{1-8}$ alkyl substituted with halogen, or $C_{1-8}$ alkoxy substituted with halogen.

(20) A compound having the formula (III) or a salt thereof, wherein $G^b$ is O.

(21) A compound having the formula (III), a salt thereof, a compound defined in (20), or a salt thereof, wherein $A^b$ is thiazole, which can be substituted with a substituent selected from the group consisting of $C_{1-8}$ alkyl, $C_{1-8}$ alkoxy, halogen, $C_{1-8}$ alkyl substituted with halogen, $C_{1-8}$ alkoxy substituted with halogen, hydroxyl, nitro, and $C_{2-8}$ acyl.

(22) A compound having the formula (III), a salt thereof, a compound defined in (20) or (21), or a salt thereof, wherein $B^b$ is ethylene chain.

(23) A compound having the formula (III), a salt thereof, a compound defined in one of (20) to (22), or a salt thereof, wherein each of $R^{1b}$ and $R^{2b}$ independently is hydrogen, $C_{1-8}$ alkyl, $C_{1-8}$ alkoxy, halogen, $C_{1-8}$ alkyl substituted with halogen, or $C_{1-8}$ alkoxy substituted with halogen.

The compound having the formula (I), (II), or (III) can be present in the form of a pharmaceutically acceptable salt. Examples of the salt include an alkali metal salt, such as sodium salt, potassium salt and lithium salt.

The compound of the present invention can also be present in the form of an optical isomer such as enantiomer or racemic body, or a geometrical isomer such as cis or trans. These isomers are included in the scope of the present invention.

The processes for preparing the compound of the formula (I) according to the invention are described below.

Synthetic Process 1 (Wherein G is O, B is Ethylene, and Z is Carboxyl)

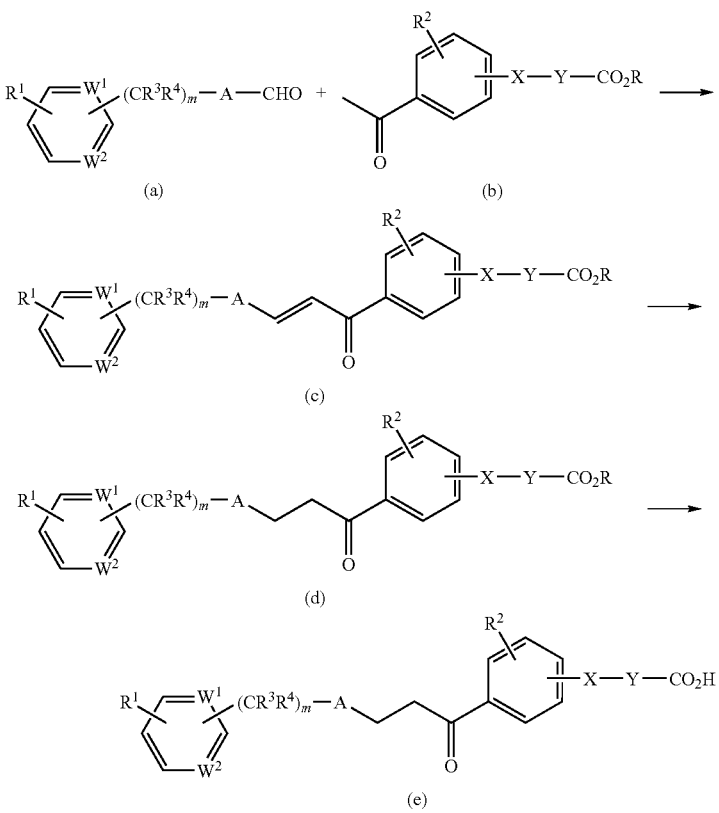

In the formulas, R is lower alkyl, and each of $W^1$, $W^2$, X, Y, A, $R^1$, $R^2$, $R^3$, $R^4$, and m are described above.

The compound of the formula (c) can be prepared by reacting the aldehyde of the formula (a) with the acetophenone derivative of the formula (b) in the presence of a base such as sodium methoxide or sodium ethoxide in an inert solvent such as THF, methanol, or ethanol.

A catalytic hydrogen reduction reaction of the obtained compound of the formula (c) is carried out in the presence of palladium-active carbon in an inert solvent such as THF or methanol to obtain an ester of the formula (d). A hydrolytic reaction of the ester of the formula (d) is carried out in the presence of lithium hydroxide or the like to obtain the compound of the formula (e) according to the present invention.

In the case that X—Y—CO$_2$H is propionic acid, an acrylic ester can be used as the compound of the formula (b). In this case, the acrylic ester is reduced to the propionic ester at the step of reducing the formula (c) to obtain the formula (d).

Synthetic Process 2 (Wherein G is CH$_2$, and Z is Carboxyl)

The ester of the formula (g) can be prepared by reacting the ketone of the formula (f) with methyl-triphenylphosphonium bromide, sodium amide in an inert solvent such as THF. A hydrolytic reaction of the ester of the formula (g) is carried out in the presence of lithium hydroxide to obtain the compound of the formula (h) according to the present invention.

Synthetic Process 3 (Wherein X is NR$^5$, and Z is Carboxyl)

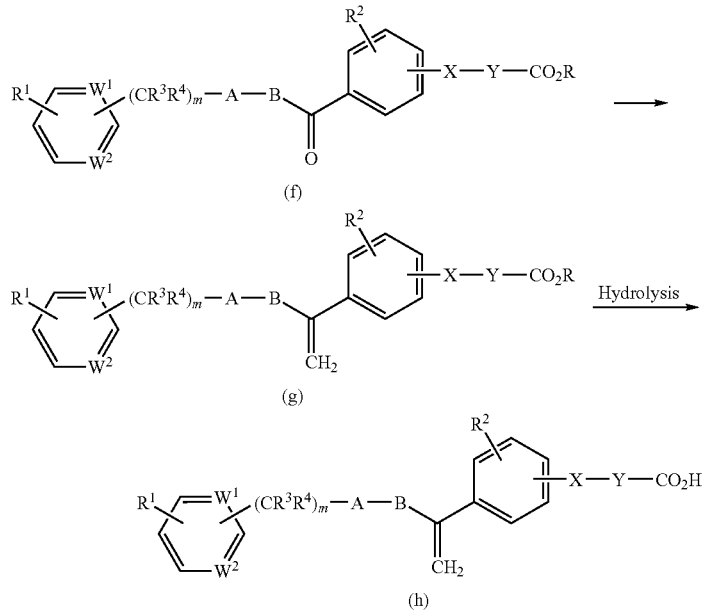

In the formulas, R is lower alkyl, and each of W$^1$, W$^2$, X, Y, A, B, R$^1$, R$^2$, R$^3$, R$^4$, and m are described above.

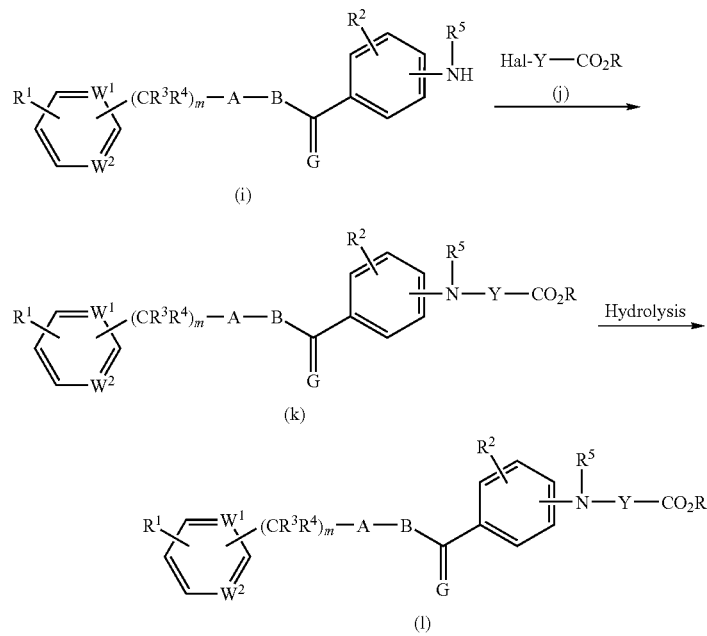

In the formulas, R is lower alkyl, hal is halogen, and each of $W^1$, $W^2$, Y, A, B, $R^1$, $R^2$, $R^3$, $R^4$, $R^5$, and m are described above.

The ester of the formula (k) can be prepared by reacting the amine of the formula (I) with the aliphatic ester of the formula (j). A hydrolytic reaction of the ester of the formula (k) is carried out to obtain the compound of (l) according to the present invention.

The amine of the formula (I) as a stating material in which $R^5$ is alkyl can be prepared according to the following reaction.

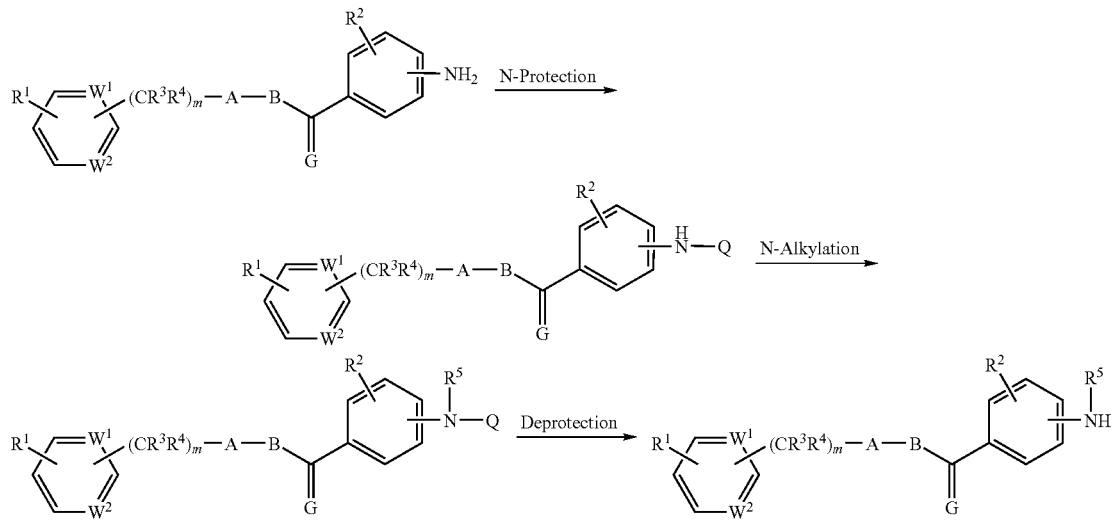

In the formulas, $R^5$ is alkyl, Q is a protective group for o-nitrobenzenesulfonyl or the like, and each of $W^1$, $W^2$, A, B, $R^1$, $R^2$, $R^3$, $R^4$, and m are described above.

The amine of the formula (I) as a stating material in which $R^5$ is H can be prepared according to the following reaction.

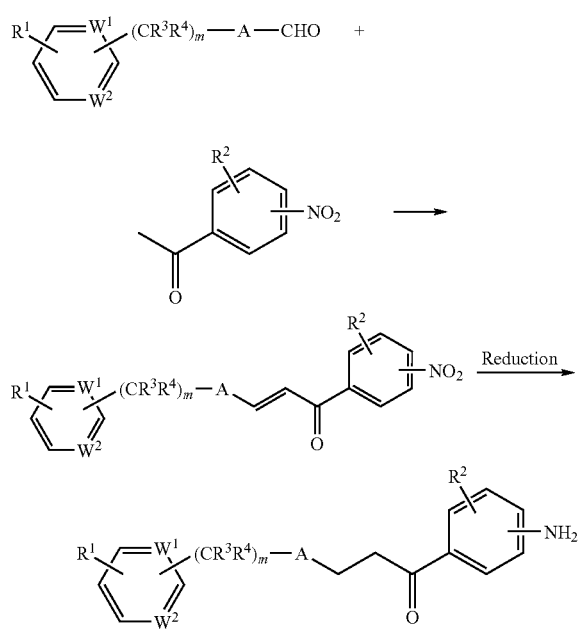

In the formulas, each of $W^1$, $W^2$, A, $R^1$, $R^2$, $R^3$, $R^4$, and m are described above.

The compound of the present invention of the formula (I), (II) or (III) can be prepared by referring to the above-mentioned synthetic processes, the below-mentioned examples, and the above-mentioned patent or known documents.

Examples of the compounds of the present invention are shown in the following Tables 1 to 37.

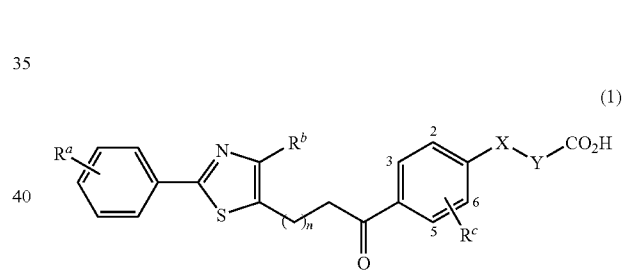

(1)

In the formula, X, Y, $R^a$, $R^b$, $R^c$, and n are set forth in Tables 1 to 3.

TABLE 1

| X | Y | $R^a$ | $R^b$ | $R^c$ | n |
|---|---|---|---|---|---|
| $CH_2$ | $CH_2$ | 4-$CF_3$ | Isopropyl | 2-$CH_3$ | 1 |
| $CH_2$ | $CH_2$ | 4-$CH_3$ | Hexyl | 2-$CH_3$ | 1 |
| $CH_2$ | $C(CH_3)_2$ | 4-$CF_3$ | Propyl | 2-$CH_3$ | 1 |
| $CH_2$ | $CH(CH_3)$ | 4-$CF_3$ | sec-Butyl | 3-$CH_3$ | 1 |
| $CH_2$ | $CH(C_2H_5)$ | 4-$CF_3$ | tert-Butyl | 3-$CH_3$ | 2 |
| $CH_2$ | CH(Propyl) | 4-$CF_3$ | Hexyl | 2,6-$CH_3$ | 3 |
| $CH_2$ | $(CH_2)_2$ | 4-$CF_3$ | Isopropyl | 2-$CH_3$ | 3 |
| $CH_2$ | $(CH_2)_2$ | 4-$CF_3$ | Cyclopropyl | 3,5-$CH_3$ | 3 |
| $CH(CH_3)$ | $CH_2$ | 4-$CF_3$ | Cyclopropylmethyl | 2-Allyl | 1 |
| $CH_2$ | $CH_2$ | 4-$CF_3$ | 4-$CF_3$-Phenyl | 2-Propyl | 2 |
| $CH_2$ | $CH_2$ | 2,4-Cl | $CH_3OCH_2CH_2$ | 2-$CH_3O$ | 2 |
| $CH_2$ | $CH_2$ | 2-OH,4-$CF_3$ | Isopropyl | 2-Cl | 1 |

TABLE 2

| X | Y | $R^a$ | $R^b$ | $R^c$ | n |
|---|---|---|---|---|---|
| CH₂ | CH₂ | 4-CH₃ | Heptyl | 2,6-CH₃ | 1 |
| NH | CH₂ | 4-CF₃ | Isopropyl | H | 1 |
| N(CH₃) | CH₂ | 4-CF₃ | Isopropyl | H | 1 |
| N(CH₃) | CH₂ | 4-CF₃ | Isopropyl | 2-CH₃ | 1 |
| N(C₂H₅) | CH₂ | 4-CF₃ | Isopropyl | 2-CH₃ | 1 |
| N(Allyl) | CH₂ | 4-CF₃ | Isopropyl | 2-CH₃ | 1 |
| N(Acetyl) | CH₂ | 2-OH,4-Cl | Isopropyl | 3-CH₃ | 3 |
| NH | CH₂ | 4-CF₃ | Isopropyl | 2-CH₃ | 1 |
| N(CH₃) | (CH₂)₂ | 4-CF₃ | Isopropyl | 2-CH₃ | 1 |
| CH₂ | CH₂ | 4-CN | Isopropyl | 2-OH | 2 |
| CH₂ | CH₂ | 4-t-Butyl | Isopropyl | 2-Acetyl | 1 |
| CH₂ | CH₂ | 4-Isopropyl | Isopropyl | 2-CF₃ | 1 |

TABLE 3

| X | Y | $R^a$ | $R^b$ | $R^c$ | n |
|---|---|---|---|---|---|
| CH₂ | (CH₂)₃ | 4-CF₃O | Butyl-OCH₂ | 2-CH₃ | 2 |
| CH₂ | CH₂ | 4-CF₃ | Butyl-OCH₂ | 2-CH₃ | 3 |
| CH₂ | CH₂ | 4-CF₃O | CH₃O(CH₂)₅ | 2-CH₃O | 3 |
| NH | CH₂ | 4-CF₃O | CH₃O(CH₂)₅ | 2-CH₃O | 1 |
| N(CH₃) | CH₂ | 4-t-Butyl | Cyclohexyl | 2-F | 2 |
| N(CH₃) | CH₂ | 4-CF₃ | Hexyl | 2-F | 1 |
| N(C₂H₅) | CH₂ | 4-CF₃ | (CH₃)₂CH(CH₂)₅ | 2,5-CH₃ | 1 |
| N(Allyl) | CH₂ | 4-CF₃ | 4-CF₃-Benzyl | 2,5-CH₃ | 1 |
| N(Ac) | CH₂ | 2,4-CH₃ | Isopropyl | 2-CH₃ | 1 |
| N(CH₃) | (CH₂)₂ | 4-Acetyl | Isopropyl | 2-CH₃ | 2 |

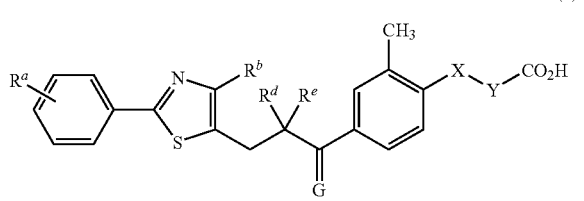

(2)

In the formula, X, Y, $R^a$, $R^b$, $R^d$, $R^e$, and G are set forth in Table 4.

TABLE 4

| X | Y | $R^a$ | $R^b$ | $R^d/R^e$ | G |
|---|---|---|---|---|---|
| CH₂ | CH₂ | 4-CF₃ | Isopropyl | H/H | CH₂ |
| CH(CH₃) | CH₂ | 4-CF₃ | Cyclopropyl-methyl | H/H | S |
| CH₂ | CH₂ | 4-CF₃ | 4-CF₃-Phenyl | H/H | C(CH₃)₂ |
| CH₂ | CH₂ | 4-CH₃ | Heptyl | H/H | CH₂ |
| NH | CH₂ | 4-CF₃ | Isopropyl | H/H | S |
| N(CH₃) | (CH₂)₂ | 4-CF₃ | Isopropyl | H/H | CH₂ |
| CH₂ | CH₂ | 4-CN | Isopropyl | H/H | C(CH₃)₂ |
| CH₂ | (CH₂)₃ | 4-CF₃O | Butyl-OCH₂ | CH₃/H | CH₂ |
| CH₂ | CH₂ | 4-CF₃O | CH₃O(CH₂)₅ | CH₃/H | O |
| N(CH₃) | CH₂ | 4-t-Butyl | Cyclohexyl | Propyl/H | O |
| N(C₂H₅) | CH₂ | 4-CF₃ | (CH₃)₂CH(CH₂)₅ | CH₃/H | O |
| N(Allyl) | CH₂ | 4-CF₃ | 4-CF₃-Benzyl | H/H | S |
| N(Acetyl) | CH₂ | 2,4-CH₃ | Isopropyl | CH₃/CH₃ | CH₂ |

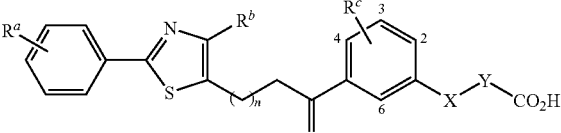

(3)

In the formula, X, Y, $R^a$, $R^b$, $R^c$, and n are set forth in Tables 5 and 6.

TABLE 5

| X | Y | $R^a$ | $R^b$ | $R^c$ | n |
|---|---|---|---|---|---|
| CH₂ | CH₂ | 4-CF₃ | Isopropyl | 2-CH₃ | 2 |
| CH₂ | CH₂ | 4-CH₃ | Hexyl | 2-CH₃ | 2 |
| CH₂ | C(CH₃)₂ | 4-CF₃ | Propyl | 2-CH₃ | 1 |
| CH₂ | CH(CH₃) | 4-CF₃ | sec-Butyl | 3-CH₃ | 1 |
| CH₂ | CH(C₂H₅) | 4-CF₃ | tert-Butyl | 3-CH₃ | 2 |
| CH₂ | CH(Propyl) | 4-CF₃ | Hexyl | 2,6-CH₃ | 3 |
| CH₂ | (CH₂)₃ | 4-CF₃ | Isopropyl | 4-CH₃ | 1 |
| CH₂ | (CH₂)₃ | 4-CF₃ | Cyclopropyl | 3,6-CH₃ | 1 |
| CH₂ | CH₂ | 2-OH,4-CF₃ | Isopropyl | 2-Cl | 1 |
| NH | CH₂ | 4-CF₃ | Isopropyl | H | 1 |

TABLE 6

| X | Y | $R^a$ | $R^b$ | $R^c$ | n |
|---|---|---|---|---|---|
| N(CH₃) | CH₂ | 4-CF₃ | Isopropyl | H | 1 |
| N(CH₃) | CH₂ | 4-CF₃ | Isopropyl | CH₃ | 1 |
| N(C₂H₅) | CH₂ | 4-CF₃ | Isopropyl | H | 1 |
| N(Allyl) | CH₂ | 4-CF₃ | Isopropyl | H | 1 |
| N(Acetyl) | CH₂ | 2-OH,4-Cl | Isopropyl | 3-CH₃ | 3 |
| CH₂ | CH₂ | 4-Isopropyl | Isopropyl | 2-CF₃ | 1 |
| CH₂ | CH₂ | 4-CF₃ | Butyl-OCH₂ | 2-CH₃ | 3 |
| NH | CH₂ | 4-CF₃O | CH₃O(CH₂)₅ | 2-CH₃O | 1 |
| N(CH₃) | CH₂ | 4-CF₃ | Hexyl | 2-F | 1 |
| N(CH₃) | (CH₂)₂ | 4-Acetyl | Isopropyl | 2-CH₃ | 2 |

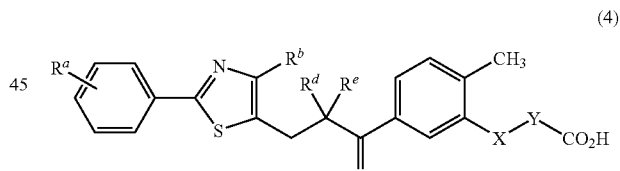

(4)

In the formula, X, Y, $R^a$, $R^b$, $R^d$, $R^e$, and G are set forth in Table 7.

TABLE 7

| X | Y | $R^a$ | $R^b$ | $R^d/R^e$ | G |
|---|---|---|---|---|---|
| CH₂ | CH₂ | 4-CF₃ | Isopropyl | H/H | CH₂ |
| CH(CH₃) | CH₂ | 4-CF₃ | Cyclopropyl-methyl | H/H | S |
| CH₂ | CH₂ | 4-CF₃ | 4-CF₃-Phenyl | H/H | C(CH₃)₂ |
| CH₂ | CH₂ | 4-CH₃ | Heptyl | H/H | CH₂ |
| NH | CH₂ | 4-CF₃ | Isopropyl | H/H | S |
| N(CH₃) | (CH₂)₂ | 4-CF₃ | Isopropyl | H/H | CH₂ |
| CH₂ | CH₂ | 4-CN | Isopropyl | H/H | C(CH₃)₂ |
| CH₂ | (CH₂)₂ | 4-CF₃O | Butyl-OCH₂ | CH₃/CH₃ | CH₂ |
| N(Allyl) | CH₂ | 4-CF₃ | 4-CF₃-Benzyl | H/H | S |
| N(Acetyl) | CH₂ | 2,4-CH₃ | Isopropyl | CH₃/CH₃ | CH₂ |

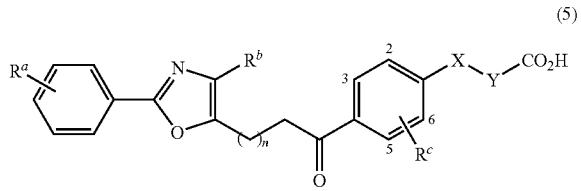

(5)

In the formula, X, Y, $R^a$, $R^b$, $R^c$, and n are set forth in Tables 8 and 9.

TABLE 8

| X | Y | $R^a$ | $R^b$ | $R^c$ | n |
|---|---|---|---|---|---|
| $CH_2$ | $CH_2$ | 4-$CF_3$ | Isopropyl | 2-$CH_3$ | 1 |
| $CH_2$ | $CH_2$ | 4-$CH_3$ | Hexyl | 2-$CH_3$ | 1 |
| $CH_2$ | $O(CH_3)_2$ | 4-$CF_3$ | Propyl | 2-$CH_3$ | 1 |
| $CH_2$ | $CH(CH_3)$ | 4-$CF_3$ | sec-Butyl | 3-$CH_3$ | 1 |
| $CH_2$ | $CH(C_2H_5)$ | 4-$CF_3$ | tert-Butyl | 3-$CH_3$ | 2 |
| $CH_2$ | $CH(Propyl)$ | 4-$CF_3$ | Hexyl | 2,6-$CH_3$ | 3 |
| $CH_2$ | $(CH_2)_2$ | 4-$CF_3$ | Isopropyl | 3-$CH_3$ | 3 |
| $CH_2$ | $(CH_2)_2$ | 4-$CF_3$ | Cyclopropyl | 3,5-$CH_3$ | 3 |
| $CH_2$ | $CH_2$ | 2-OH,4-$CF_3$ | Isopropyl | 2-Cl | 1 |
| NH | $CH_2$ | 4-$CF_3$ | Isopropyl | H | 1 |

TABLE 9

| X | Y | $R^a$ | $R^b$ | $R^c$ | n |
|---|---|---|---|---|---|
| $N(CH_3)$ | $CH_2$ | 4-$CF_3$ | Isopropyl | H | 1 |
| $N(CH_3)$ | $CH_2$ | 4-$CF_3$ | Isopropyl | 2-$CH_3$ | 1 |
| $N(C_2H_5)$ | $CH_2$ | 4-$CF_3$ | Isopropyl | H | 1 |
| $N(Allyl)$ | $CH_2$ | 4-$CF_3$ | Isopropyl | H | 1 |
| $N(Acetyl)$ | $CH_2$ | 2-OH,4-Cl | Isopropyl | H | 3 |
| $CH_2$ | $CH_2$ | 4-Isopropyl | Isopropyl | 2-$CF_3$ | 1 |
| $CH_2$ | $CH_2$ | 4-$CF_3$ | Butyl-$OCH_2$ | 2-$CH_3$ | 3 |
| NH | $CH_2$ | 4-$CF_3O$ | $CH_3O(CH_2)_5$ | 2-$CH_3O$ | 1 |
| $N(CH_3)$ | $CH_2$ | 4-$CF_3$ | Hexyl | 2-F | 1 |
| $N(CH_3)$ | $(CH_2)_2$ | 4-Acetyl | Isopropyl | 2-$CH_3$ | 2 |

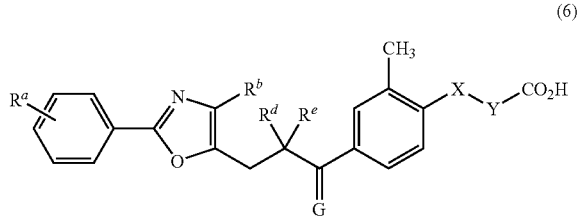

(6)

In the formula, X, Y, $R^a$, $R^d$, $R^e$, and G are set forth in Table 10.

TABLE 10

| X | Y | $R^a$ | $R^b$ | $R^d/R^e$ | G |
|---|---|---|---|---|---|
| $CH_2$ | $CH_2$ | 4-$CF_3$ | Isopropyl | H/H | $CH_2$ |
| $CH(CH_3)$ | $CH_2$ | 4-$CF_3$ | Cyclopropyl-methyl | H/H | S |
| $CH_2$ | $CH_2$ | 4-$CF_3$ | 4-$CF_3$-Phenyl | H/H | $C(CH_3)_2$ |
| $CH_2$ | $CH_2$ | 2,4-Cl | $CH_3OCH_2CH_2$ | $CH_3$/H | O |
| $CH_2$ | $CH_2$ | 4-$CH_3$ | Heptyl | H/H | $CH_2$ |
| NH | $CH_2$ | 4-$CF_3$ | Isopropyl | H/H | S |
| $N(CH_3)$ | $(CH_2)_2$ | 4-$CF_3$ | Isopropyl | H/H | $CH_2$ |
| $CH_2$ | $CH_2$ | 4-CN | Isopropyl | H/H | $C(CH_3)_2$ |
| $CH_2$ | $CH_2$ | 4-t-Butyl | Isopropyl | $C_2H_5$/H | O |

TABLE 10-continued

| X | Y | $R^a$ | $R^b$ | $R^d/R^e$ | G |
|---|---|---|---|---|---|
| $CH_2$ | $(CH_2)_3$ | 4-$CF_3O$ | Butyl-$OCH_2$ | $CH_3$/$CH_3$ | $CH_2$ |
| $CH_2$ | $CH_2$ | 4-$CF_3O$ | $CH_3O(CH_2)_5$ | $CH_3$/$CH_3$ | O |
| $N(CH_3)$ | $CH_2$ | 4-t-Butyl | Cyclohexyl | $CH_3$/$CH_3$ | O |
| $N(C_2H_5)$ | $CH_2$ | 4-$CF_3$ | $(CH_3)_2CH(CH_2)_5$ | $CH_3$/$CH_3$ | O |
| $N(Allyl)$ | $CH_2$ | 4-$CF_3$ | 4-$CF_3$-Benzyl | H/H | S |
| $N(Acetyl)$ | $CH_2$ | 2,4-$CH_3$ | Isopropyl | $CH_3$/$CH_3$ | $CH_2$ |

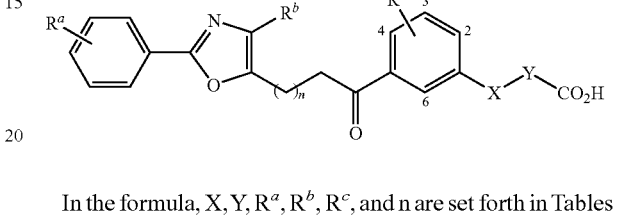

(7)

In the formula, X, Y, $R^a$, $R^b$, $R^c$, and n are set forth in Tables 11 to 13.

TABLE 11

| X | Y | $R^a$ | $R^b$ | $R^c$ | n |
|---|---|---|---|---|---|
| $CH_2$ | $CH_2$ | 4-$CF_3$ | Isopropyl | 2-$CH_3$ | 1 |
| $CH_2$ | $CH_2$ | 4-$CH_3$ | Hexyl | 2-$CH_3$ | 1 |
| $CH_2$ | $CH_2$ | 4-$CF_3$ | Isopropyl | 2-$CH_3$ | 2 |
| $CH_2$ | $C(CH_3)_2$ | 4-$CF_3$ | Propyl | 2-$CH_3$ | 1 |
| $CH_2$ | $CH(CH_3)$ | 4-$CF_3$ | sec-Butyl | 3-$CH_3$ | 1 |
| $CH_2$ | $CH(C_2H_5)$ | 4-$CF_3$ | tert-Butyl | 3-$CH_3$ | 2 |
| $CH_2$ | $CH(Propyl)$ | 4-$CF_3$ | Hexyl | 2,6-$CH_3$ | 3 |
| $CH_2$ | $(CH_2)_2$ | 4-$CF_3$ | Isopropyl | 2-$CH_3$ | 1 |
| $CH_2$ | $(CH_2)_2$ | 4-$CF_3$ | Cyclopropyl | 3,4-$CH_3$ | 3 |
| $CH(CH_3)$ | $CH_2$ | 4-$CF_3$ | Cyclopropylmethyl | 2-Allyl | 1 |
| $CH_2$ | $CH_2$ | 4-$CF_3$ | 4-$CF_3$-Phenyl | 2-Propyl | 2 |
| $CH_2$ | $CH_2$ | 2,4-Cl | $CH_3OCH_2CH_2$ | 2-$CH_3O$ | 2 |

TABLE 12

| X | Y | $R^a$ | $R^b$ | $R^c$ | n |
|---|---|---|---|---|---|
| $CH_2$ | $CH_2$ | 2-OH,4-$CF_3$ | Isopropyl | 2-Cl | 1 |
| $CH_2$ | $CH_2$ | 4-$CH_3$ | Heptyl | 2,6-$CH_3$ | 1 |
| NH | $CH_2$ | 4-$CF_3$ | Isopropyl | H | 1 |
| $N(CH_3)$ | $CH_2$ | 4-$CF_3$ | Isopropyl | H | 1 |
| $N(CH_3)$ | $CH_2$ | 4-$CF_3$ | Isopropyl | 2-$CH_3$ | 1 |
| $N(C_2H_5)$ | $CH_2$ | 4-$CF_3$ | Isopropyl | H | 1 |
| $N(Allyl)$ | $CH_2$ | 4-$CF_3$ | Isopropyl | H | 1 |
| $N(Acetyl)$ | $CH_2$ | 2-OH,4-Cl | Isopropyl | H | 3 |
| NH | $CH_2$ | 4-$CF_3$ | Isopropyl | 2-$CH_3$ | 1 |
| $N(CH_3)$ | $(CH_2)_2$ | 4-$CF_3$ | Isopropyl | 2-$CH_3$ | 1 |
| $CH_2$ | $CH_2$ | 4-CN | Isopropyl | 2-OH | 2 |
| $CH_2$ | $CH_2$ | 4-t-Butyl | Isopropyl | 2-Acetyl | 1 |

TABLE 13

| X | Y | $R^a$ | $R^b$ | $R^c$ | n |
|---|---|---|---|---|---|
| $CH_2$ | $CH_2$ | 4-Isopropyl | Isopropyl | 2-$CF_3$ | 1 |
| $CH_2$ | $(CH_2)_3$ | 4-$CF_3O$ | Butyl-$OCH_2$ | 2-$CH_3$ | 2 |
| $CH_2$ | $CH_2$ | 4-$CF_3$ | Butyl-$OCH_2$ | 2-$CH_3$ | 3 |
| $CH_2$ | $CH_2$ | 4-$CF_3O$ | $CH_3O(CH_2)_5$ | 2-$CH_3O$ | 3 |
| NH | $CH_2$ | 4-$CF_3O$ | $CH_3O(CH_2)_5$ | 2-$CH_3O$ | 1 |
| $N(CH_3)$ | $CH_2$ | 4-t-Butyl | Cyclohexyl | 2-F | 2 |
| $N(CH_3)$ | $CH_2$ | 4-$CF_3$ | Hexyl | 2-F | 1 |
| $N(C_2H_5)$ | $CH_2$ | 4-$CF_3$ | $(CH_3)_2CH(CH_2)_5$ | 2,6-$CH_3$ | 1 |
| $N(Allyl)$ | $CH_2$ | 4-$CF_3$ | 4-$CF_3$-Benzyl | 2,6-$CH_3$ | 1 |

TABLE 13-continued

| X | Y | $R^a$ | $R^b$ | $R^c$ | n |
|---|---|---|---|---|---|
| N(Acetyl) | $CH_2$ | 2,4-$CH_3$ | Isopropyl | 2-$CH_3$ | 1 |
| N($CH_3$) | $(CH_2)_2$ | 4-Acetyl | Isopropyl | 2-$CH_3$ | 2 |

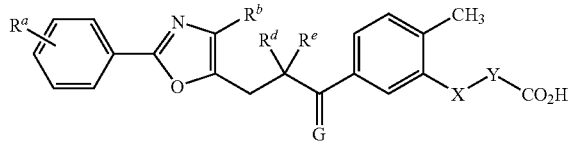

(8)

In the formula, X, Y, $R^a$, $R^b$, $R^d$, $R^e$, and G are set forth in Table 14.

TABLE 14

| X | Y | $R^a$ | $R^b$ | $R^d/R^e$ | G |
|---|---|---|---|---|---|
| $CH_2$ | $CH_2$ | 4-$CF_3$ | Isopropyl | H/H | $CH_2$ |
| $CH(CH_3)$ | $CH_2$ | 4-$CF_3$ | Cyclopropyl-methyl | H/H | S |
| $CH_2$ | $CH_2$ | 4-$CF_3$ | 4-$CF_3$-Phenyl | H/H | $C(CH_3)_2$ |
| $CH_2$ | $CH_2$ | 2,4-Cl | $CH_3OCH_2CH_2$ | $CH_3$/H | O |
| $CH_2$ | $CH_2$ | 4-$CH_3$ | Heptyl | H/H | $CH_2$ |
| NH | $CH_2$ | 4-$CF_3$ | Isopropyl | H/H | S |
| N($CH_3$) | $(CH_2)_2$ | 4-$CF_3$ | Isopropyl | H/H | $CH_2$ |
| $CH_2$ | $CH_2$ | 4-CN | Isopropyl | H/H | $C(CH_3)_2$ |
| $CH_2$ | $CH_2$ | 4-t-Butyl | Isopropyl | $C_2H_5$/H | O |
| $CH_2$ | $(CH_2)_3$ | 4-$CF_3O$ | Butyl-$OCH_2$ | $CH_3$/H | $CH_2$ |
| $CH_2$ | $CH_2$ | 4-$CF_3O$ | $CH_3O(CH_2)_5$ | $CH_3$/H | O |
| N($CH_3$) | $CH_2$ | 4-t-Butyl | Cyclohexyl | $CH_3$/H | O |
| N($C_2H_5$) | $CH_2$ | 4-$CF_3$ | $(CH_3)_2CH(CH_2)_5$ | $CH_3/CH_3$ | O |
| N(Allyl) | $CH_2$ | 4-$CF_3$ | 4-$CF_3$-Benzyl | H/H | S |
| N(Acetyl) | $CH_2$ | 2,4-$CH_3$ | Isopropyl | $CH_3/CH_3$ | $CH_2$ |

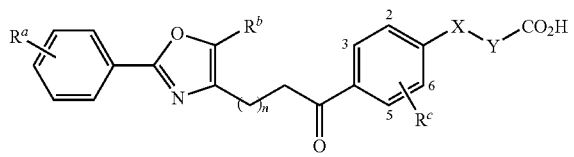

(9)

In the formula, X, Y, $R^a$, $R^b$, $R^c$, and n are set forth in Tables 15 to 17.

TABLE 15

| X | Y | $R^a$ | $R^b$ | $R^c$ | n |
|---|---|---|---|---|---|
| $CH_2$ | $CH_2$ | H | Isopropyl | 2-$CH_3$ | 1 |
| $CH_2$ | $CH_2$ | 2-OH,4-Cl | Hexyl | 2-$CH_3$ | 1 |
| $CH_2$ | $CH_2$ | 2-OH,4-$CF_3$ | Isopropyl | 2-$CH_3$ | 1 |
| $CH_2$ | $C(CH_3)_2$ | 2,4-Cl | Propyl | 2-$CH_3$ | 1 |
| $CH_2$ | $CH(CH_3)$ | 4-$CF_3$ | sec-Butyl | 3-$CH_3$ | 1 |
| $CH_2$ | $CH(C_2H_5)$ | 4-$CF_3$ | tert-Butyl | 3-$CH_3$ | 2 |
| $CH_2$ | $CH(Propyl)$ | 4-$CF_3$ | Hexyl | 2,6-$CH_3$ | 3 |
| $CH_2$ | $(CH_2)_2$ | 4-$CF_3$ | Isopropyl | 3-$CH_3$ | 3 |
| $CH_2$ | $(CH_2)_2$ | 4-$CF_3$ | Cyclopropyl | 3,5-$CH_3$ | 3 |
| $CH(CH_3)$ | $CH_2$ | 4-$CF_3$ | Cyclopropyl-methyl | 2-Allyl | 1 |
| $CH_2$ | $CH_2$ | 4-$CF_3$ | 4-$CF_3$-Phenyl | 2-Propyl | 2 |
| $CH_2$ | $CH_2$ | 2,4-Cl | $CH_3OCH_2CH_2$ | 2-$CH_3O$ | 2 |

TABLE 16

| X | Y | $R^a$ | $R^b$ | $R^c$ | n |
|---|---|---|---|---|---|
| $CH_2$ | $CH_2$ | 2-OH,4-$CF_3$ | Isopropyl | 2-Cl | 1 |
| $CH_2$ | $CH_2$ | 4-$CH_3$ | Heptyl | 2,6-$CH_3$ | 1 |
| NH | $CH_2$ | 4-$CF_3$ | Isopropyl | H | 1 |
| N($CH_3$) | $CH_2$ | 4-$CF_3$ | Isopropyl | H | 1 |
| N($CH_3$) | $CH_2$ | 4-$CF_3$ | Isopropyl | 2-$CH_3$ | 1 |
| N($C_2H_5$) | $CH_2$ | 4-$CF_3$ | Isopropyl | H | 1 |
| N(Allyl) | $CH_2$ | 4-$CF_3$ | Isopropyl | H | 1 |
| N($CH_3$) | $CH_2$ | 2-OH,4-Cl | Isopropyl | H | 1 |
| NH | $CH_2$ | 4-$CF_3$ | Isopropyl | 2-$CH_3$ | 1 |
| N($CH_3$) | $(CH_2)_2$ | 4-$CF_3$ | Isopropyl | 2-$CH_3$ | 1 |
| $CH_2$ | $CH_2$ | 4-CN | Isopropyl | 2-OH | 2 |
| $CH_2$ | $CH_2$ | 4-t-Butyl | Isopropyl | 2-Acetyl | 1 |

TABLE 17

| X | Y | $R^a$ | $R^b$ | $R^c$ | n |
|---|---|---|---|---|---|
| $CH_2$ | $CH_2$ | 4-Isopropyl | Isopropyl | 2-$CF_3$ | 1 |
| $CH_2$ | $(CH_2)_3$ | 4-$CF_3O$ | Butyl-$OCH_2$ | 2-$CH_3$ | 2 |
| $CH_2$ | $CH_2$ | 4-$CF_3$ | Butyl-$OCH_2$ | 2-$CH_3$ | 3 |
| $CH_2$ | $CH_2$ | 4-$CF_3O$ | $CH_3O(CH_2)_5$ | 2-$CH_3O$ | 3 |
| NH | $CH_2$ | 4-$CF_3O$ | $CH_3O(CH_2)_5$ | 2-$CH_3O$ | 1 |
| N($CH_3$) | $CH_2$ | 4-t-Butyl | Cyclohexyl | 2-F | 2 |
| N($CH_3$) | $CH_2$ | 4-$CF_3$ | Hexyl | 2-F | 1 |
| N($C_2H_5$) | $CH_2$ | 4-$CF_3$ | $(CH_3)_2CH(CH_2)_5$ | 2,5-$CH_3$ | 1 |
| N(Allyl) | $CH_2$ | 4-$CF_3$ | 4-$CF_3$-Benzyl | 2,5-$CH_3$ | 1 |
| N(Acetyl) | $CH_2$ | 2,4-$CH_3$ | Isopropyl | 2-$CH_3$ | 1 |
| N($CH_3$) | $(CH_2)_2$ | 4-Acetyl | Isopropyl | 2-$CH_3$ | 2 |

(10)

In the formula, X, Y, $R^a$, $R^b$, $R^d$, $R^e$, and G are set forth in Table 18.

TABLE 18

| X | Y | $R^a$ | $R^b$ | $R^d/R^e$ | G |
|---|---|---|---|---|---|
| $CH_2$ | $CH_2$ | 2-OH,4-$CF_3$ | Isopropyl | H/H | $CH_2$ |
| $CH(CH_3)$ | $CH_2$ | 4-$CF_3$ | Cyclopropyl-methyl | H/H | S |
| $CH_2$ | $CH_2$ | 4-$CF_3$ | 4-$CF_3$-Phenyl | H/H | $C(CH_3)_2$ |
| $CH_2$ | $CH_2$ | 2,4-Cl | $CH_3OCH_2CH_2$ | $CH_3$/H | O |
| $CH_2$ | $CH_2$ | 4-$CH_3$ | Heptyl | H/H | $CH_2$ |
| NH | $CH_2$ | 4-$CF_3$ | Isopropyl | H/H | S |
| N($CH_3$) | $(CH_2)_2$ | 4-$CF_3$ | Isopropyl | H/H | $CH_2$ |
| $CH_2$ | $CH_2$ | 4-CN | Isopropyl | H/H | $C(CH_3)_2$ |
| $CH_2$ | $CH_2$ | 4-t-Butyl | Isopropyl | $C_2H_5$/H | O |
| $CH_2$ | $(CH_2)_3$ | 4-$CF_3O$ | Butyl-$OCH_2$ | $CH_3/CH_3$ | $CH_2$ |
| $CH_2$ | $CH_2$ | 4-$CF_3O$ | $CH_3O(CH_2)_5$ | $CH_3/CH_3$ | O |
| N($CH_3$) | $CH_2$ | 4-t-Butyl | Cyclohexyl | $CH_3/CH_3$ | O |
| N($C_2H_5$) | $CH_2$ | 4-$CF_3$ | $(CH_3)_2CH(CH_2)_5$ | $CH_3/CH_3$ | O |
| N(Allyl) | $CH_2$ | 4-$CF_3$ | 4-$CF_3$-Benzyl | H/H | S |
| N(Acetyl) | $CH_2$ | 2,4-$CH_3$ | Isopropyl | $CH_3/CH_3$ | $CH_2$ |

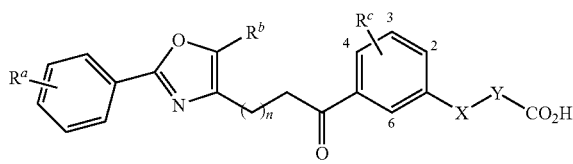

(11)

In the formula, X, Y, $R^a$, $R^b$, $R^c$, and n are set forth in Tables 19 and 20.

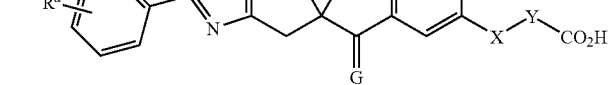

(12)

In the formula, X, Y, $R^a$, $R^b$, $R^d$, $R^e$, and G are set forth in Table 21.

TABLE 21

| X | Y | $R^a$ | $R^b$ | $R^d$/$R^e$ | G |
|---|---|---|---|---|---|
| $CH_2$ | $CH_2$ | 2-OH,4-$CF_3$ | Isopropyl | H/H | $CH_2$ |
| $CH(CH_3)$ | $CH_2$ | 4-$CF_3$ | Cyclopropylmethyl | H/H | S |
| $CH_2$ | $CH_2$ | 4-$CF_3$ | 4-$CF_3$-Phenyl | H/H | $C(CH_3)_2$ |
| $CH_2$ | $CH_2$ | 2,4-Cl | $CH_3OCH_2CH_2$ | $CH_3$/H | O |
| $CH_2$ | $CH_2$ | 4-$CH_3$ | Heptyl | H/H | $CH_2$ |
| NH | $CH_2$ | 4-$CF_3$ | Isopropyl | H/H | S |
| $N(CH_3)$ | $(CH_2)_2$ | 4-$CF_3$ | Isopropyl | H/H | $CH_2$ |
| $CH_2$ | $CH_2$ | 4-CN | Isopropyl | H/H | $C(CH_3)_2$ |
| $CH_2$ | $CH_2$ | 4-t-Butyl | Isopropyl | $C_2H_5$/H | O |
| $CH_2$ | $(CH_2)_3$ | 4-$CF_3O$ | Butyl-$OCH_2$ | $CH_3$/$CH_3$ | $CH_2$ |
| $CH_2$ | $CH_2$ | 4-$CF_3O$ | $CH_3O(CH_2)_5$ | $CH_3$/$CH_3$ | O |
| $N(CH_3)$ | $CH_2$ | 4-t-Butyl | Cyclohexyl | $CH_3$/$CH_3$ | O |
| $N(C_2H_5)$ | $CH_2$ | 4-$CF_3$ | $(CH_3)_2CH(CH_2)_5$ | $CH_3$/$CH_3$ | O |
| N(Allyl) | $CH_2$ | 4-$CF_3$ | 4-$CF_3$-Benzyl | H/H | S |
| N(Acetyl) | $CH_2$ | 2,4-$CH_3$ | Isopropyl | $CH_3$/$CH_3$ | $CH_2$ |

TABLE 19

| X | Y | $R^a$ | $R^b$ | $R^c$ | n |
|---|---|---|---|---|---|
| $CH_2$ | $CH_2$ | H | Isopropyl | 2-$CH_3$ | 1 |
| $CH_2$ | $CH_2$ | 2-OH,4-Cl | Hexyl | 2-$CH_3$ | 1 |
| $CH_2$ | $C(CH_3)_2$ | 2,4-Cl | Propyl | 2-$CH_3$ | 1 |
| $CH_2$ | $CH(CH_3)$ | 4-$CF_3$ | sec-Butyl | 3-$CH_3$ | 1 |
| $CH_2$ | $CH(C_2H_5)$ | 4-$CF_3$ | tert-Butyl | 3-$CH_3$ | 2 |
| $CH_2$ | CH(Propyl) | 4-$CF_3$ | Hexyl | 2,6-$CH_3$ | 3 |
| $CH_2$ | $(CH_2)_2$ | 4-$CF_3$ | Isopropyl | 3-$CH_3$ | 3 |
| $CH_2$ | $(CH_2)_2$ | 4-$CF_3$ | Cyclopropyl | 3,6-$CH_3$ | 3 |
| $CH_2$ | $CH_2$ | 2-OH,4-$CF_3$ | Isopropyl | 2-Cl | 1 |
| NH | $CH_2$ | 4-$CF_3$ | Isopropyl | H | 1 |

TABLE 20

| X | Y | $R^a$ | $R^b$ | $R^c$ | n |
|---|---|---|---|---|---|
| $N(CH_3)$ | $CH_2$ | 4-$CF_3$ | Isopropyl | H | 1 |
| $N(CH_3)$ | $CH_2$ | 4-$CF_3$ | Isopropyl | 2-$CH_3$ | 1 |
| $N(C_2H_5)$ | $CH_2$ | 4-$CF_3$ | Isopropyl | H | 1 |
| N(Allyl) | $CH_2$ | 4-$CF_3$ | Isopropyl | H | 1 |
| N(Acetyl) | $CH_2$ | 2-OH,4-Cl | Isopropyl | H | 3 |
| $CH_2$ | $CH_2$ | 4-Isopropyl | Isopropyl | 2-$CF_3$ | 1 |
| $CH_2$ | $CH_2$ | 4-$CF_3$ | Butyl-$OCH_2$ | 2-$CH_3$ | 3 |
| NH | $CH_2$ | 4-$CF_3O$ | $CH_3O(CH_2)_5$ | 2-$CH_3O$ | 1 |
| $N(CH_3)$ | $CH_2$ | 4-$CF_3$ | Hexyl | 2-F | 1 |
| $N(CH_3)$ | $(CH_2)_2$ | 4-Acetyl | Isopropyl | 2-$CH_3$ | 2 |

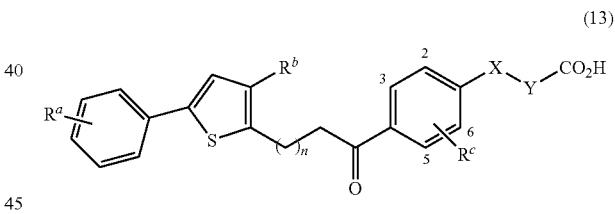

(13)

In the formula, X, Y, $R^a$, $R^b$, $R^c$, and n are set forth in Tables 22 and 23.

TABLE 22

| X | Y | $R^a$ | $R^b$ | $R^c$ | n |
|---|---|---|---|---|---|
| $CH_2$ | $CH_2$ | 4-$CF_3$ | Isopropyl | 2-$CH_3$ | 1 |
| $CH_2$ | $CH_2$ | 2-OH,4-Cl | Hexyl | 2-$CH_3$ | 1 |
| $CH_2$ | $C(CH_3)_2$ | 2,4-Cl | Propyl | 2-$CH_3$ | 1 |
| $CH_2$ | $CH(CH_3)$ | 4-$CF_3$ | sec-Butyl | 3-$CH_3$ | 1 |
| $CH_2$ | $CH(C_2H_5)$ | 4-$CF_3$ | tert-Butyl | 3-$CH_3$ | 2 |
| $CH_2$ | CH(Propyl) | 4-$CF_3$ | Hexyl | 2,6-$CH_3$ | 3 |
| $CH_2$ | $(CH_2)_2$ | 4-$CF_3$ | Isopropyl | 3-$CH_3$ | 3 |
| $CH_2$ | $(CH_2)_2$ | 4-$CF_3$ | Cyclopropyl | 3,5-$CH_3$ | 3 |
| $CH_2$ | $CH_2$ | 2-OH,4-$CF_3$ | Isopropyl | 2-Cl | 1 |
| NH | $CH_2$ | 4-$CF_3$ | Isopropyl | H | 1 |
| $N(CH_3)$ | $CH_2$ | 4-$CF_3$ | Isopropyl | H | 1 |

TABLE 23

| X | Y | $R^a$ | $R^b$ | $R^c$ | n |
|---|---|---|---|---|---|
| N(CH$_3$) | CH$_2$ | 4-CF$_3$ | Isopropyl | 2-CH$_3$ | 1 |
| N(C$_2$H$_5$) | CH$_2$ | 4-CF$_3$ | Isopropyl | H | 1 |
| N(Allyl) | CH$_2$ | 4-CF$_3$ | Isopropyl | H | 1 |
| N(Acetyl) | CH$_2$ | 2-OH,4-Cl | Isopropyl | H | 3 |
| N(CH$_3$) | CH$_2$ | 4-CF$_3$ | Isopropyl | 2-CH$_3$ | 1 |
| CH$_2$ | CH$_2$ | 4-Isopropyl | Isopropyl | 2-CF$_3$ | 1 |
| CH$_2$ | CH$_2$ | 4-CF$_3$ | Butyl-OCH$_2$ | 2-CH$_3$ | 3 |
| NH | CH$_2$ | 4-CF$_3$O | CH$_3$O(CH$_2$)$_5$ | 2-CH$_3$O | 1 |
| N(CH$_3$) | CH$_2$ | 4-CF$_3$ | Hexyl | 2-F | 1 |
| N(CH$_3$) | (CH$_2$)$_2$ | 4-Acetyl | Isopropyl | 2-CH$_3$ | 2 |

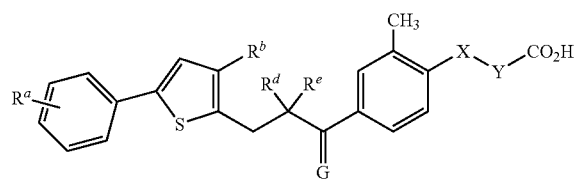

(14)

In the formula, X, Y, $R^a$, $R^b$, $R^d$, $R^e$, and G are set forth in Table 24.

TABLE 24

| X | Y | $R^a$ | $R^b$ | $R^d/R^e$ | G |
|---|---|---|---|---|---|
| CH$_2$ | CH$_2$ | 2-OH,4-CF$_3$ | Isopropyl | H/H | CH$_2$ |
| CH(CH$_3$) | CH$_2$ | 4-CF$_3$ | Cyclopropylmethyl | H/H | S |
| CH$_2$ | CH$_2$ | 4-CF$_3$ | 4-CF$_3$-Phenyl | H/H | C(CH$_3$)$_2$ |
| CH$_2$ | CH$_2$ | 2,4-Cl | CH$_3$OCH$_2$CH$_2$ | CH$_3$/H | O |
| CH$_2$ | CH$_2$ | 4-CH$_3$ | Heptyl | H/H | CH$_2$ |
| NH | CH$_2$ | 4-CF$_3$ | Isopropyl | H/H | S |
| N(CH$_3$) | (CH$_2$)$_2$ | 4-CF$_3$ | Isopropyl | H/H | CH$_2$ |
| CH$_2$ | CH$_2$ | 4-CN | Isopropyl | H/H | C(CH$_3$)$_2$ |
| CH$_2$ | CH$_2$ | 4-t-Butyl | Isopropyl | C$_2$H$_5$/H | O |
| CH$_2$ | (CH$_2$)$_3$ | 4-CF$_3$O | Butyl-OCH$_2$ | CH$_3$/CH$_3$ | CH$_2$ |
| CH$_2$ | CH$_2$ | 4-CF$_3$O | CH$_3$O(CH$_2$)$_5$ | CH$_3$/CH$_3$ | O |
| N(CH$_3$) | CH$_2$ | 4-t-Butyl | Cyclohexyl | CH$_3$/CH$_3$ | O |
| N(C$_2$H$_5$) | CH$_2$ | 4-CF$_3$ | (CH$_3$)$_2$CH(CH$_2$)$_5$ | CH$_3$/CH$_3$ | O |
| N(Allyl) | CH$_2$ | 4-CF$_3$ | 4-CF$_3$-Benzyl | H/H | S |
| N(Acetyl) | CH$_2$ | 2,4-CH$_3$ | Isopropyl | CH$_3$/CH$_3$ | CH$_2$ |

TABLE 25

| X | Y | $R^a$ | $R^b$ | $R^c$ | n |
|---|---|---|---|---|---|
| CH$_2$ | CH$_2$ | 4-CF$_3$ | Isopropyl | 2-CH$_3$ | 1 |
| CH$_2$ | CH$_2$ | 2-OH,4-Cl | Hexyl | 2-CH$_3$ | 1 |
| CH$_2$ | C(CH$_3$)$_2$ | 2,4-Cl | Propyl | 2-CH$_3$ | 1 |
| CH$_2$ | CH(CH$_3$) | 4-CF$_3$ | sec-Butyl | 3-CH$_3$ | 1 |
| CH$_2$ | CH(C$_2$H$_5$) | 4-CF$_3$ | tert-Butyl | 3-CH$_3$ | 2 |
| CH$_2$ | CH(Propyl) | 4-CF$_3$ | Hexyl | 2,6-CH$_3$ | 3 |
| CH$_2$ | (CH$_2$)$_2$ | 4-CF$_3$ | Isopropyl | 3-CH$_3$ | 3 |
| CH$_2$ | (CH$_2$)$_2$ | 4-CF$_3$ | Cyclopropyl | 3,6-CH$_3$ | 3 |
| CH$_2$ | CH$_2$ | 2-OH,4-CF$_3$ | Isopropyl | 2-Cl | 1 |
| NH | CH$_2$ | 4-CF$_3$ | Isopropyl | H | 1 |
| N(CH$_3$) | CH$_2$ | 4-CF$_3$ | Isopropyl | H | 1 |

TABLE 26

| X | Y | $R^a$ | $R^b$ | $R^c$ | n |
|---|---|---|---|---|---|
| N(CH$_3$) | CH$_2$ | 4-CF$_3$ | Isopropyl | 2-CH$_3$ | 1 |
| N(C$_2$H$_5$) | CH$_2$ | 4-CF$_3$ | Isopropyl | 2-CH$_3$ | 1 |
| N(Allyl) | CH$_2$ | 4-CF$_3$ | Isopropyl | 2-CH$_3$ | 1 |
| N(Acetyl) | CH$_2$ | 2-OH,4-Cl | Isopropyl | 3-CH$_3$ | 3 |
| CH$_2$ | CH$_2$ | 4-Isopropyl | Isopropyl | 2-CF$_3$ | 1 |
| CH$_2$ | CH$_2$ | 4-CF$_3$ | Butyl-OCH$_2$ | 2-CH$_3$ | 3 |
| NH | CH$_2$ | 4-CF$_3$O | CH$_3$O(CH$_2$)$_5$ | 2-CH$_3$O | 1 |
| N(CH$_3$) | CH$_2$ | 4-CF$_3$ | Hexyl | 2-F | 1 |
| N(CH$_3$) | (CH$_2$)$_2$ | 4-Acetyl | Isopropyl | 2-CH$_3$ | 2 |

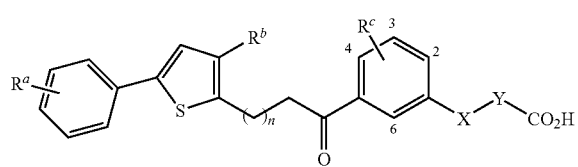

(15)

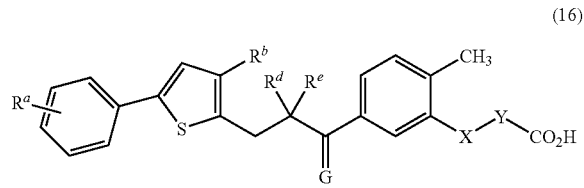

(16)

In the formula, X, Y, $R^a$, $R^b$, $R^c$, and n are set forth in Tables 25 and 26.

In the formula, X, Y, $R^a$, $R^b$, $R^d$, $R^e$, and G are set forth in Table 27.

TABLE 27

| X | Y | $R^a$ | $R^b$ | $R^d/R^e$ | G |
|---|---|---|---|---|---|
| CH₂ | CH₂ | 2-OH,4-CF₃ | Isopropyl | H/H | CH₂ |
| CH(CH₃) | CH₂ | 4-CF₃ | Cyclopropylmethyl | H/H | S |
| CH₂ | CH₂ | 4-CF₃ | 4-CF₃-Phenyl | H/H | C(CH₃)₂ |
| CH₂ | CH₂ | 2,4-Cl | CH₃OCH₂CH₂ | CH₃/H | O |
| CH₂ | CH₂ | 4-CH₃ | Heptyl | H/H | CH₂ |
| NH | CH₂ | 4-CF₃ | Isopropyl | H/H | S |
| N(CH₃) | (CH₂)₂ | 4-CF₃ | Isopropyl | H/H | CH₂ |
| CH₂ | CH₂ | 4-CN | Isopropyl | H/H | C(CH₃)₂ |
| CH₂ | CH₂ | 4-t-Butyl | Isopropyl | C₂H₅/H | O |
| CH₂ | (CH₂)₃ | 4-CF₃O | Butyl-OCH₂ | CH₃/CH₃ | CH₂ |
| CH₂ | CH₂ | 4-CF₃O | CH₃O(CH₂)₅ | CH₃/CH₃ | O |
| N(CH₃) | CH₂ | 4-t-Butyl | Cyclohexyl | CH₃/CH₃ | O |
| N(C₂H₅) | CH₂ | 4-CF₃ | (CH₃)₂CH(CH₂)₅ | CH₃/CH₃ | O |
| N(Allyl) | CH₂ | 4-CF₃ | 4-CF₃-Benzyl | H/H | S |
| N(Acetyl) | CH₂ | 2,4-CH₃ | Isopropyl | CH₃/CH₃ | CH₂ |

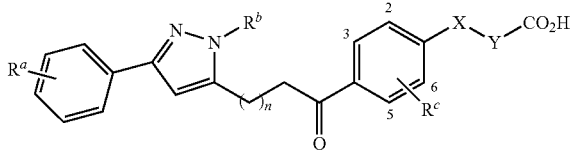

(17)

In the formula, X, Y, $R^a$, $R^b$, $R^c$, and n are set forth in Tables 28 and 29.

TABLE 28

| X | Y | $R^a$ | $R^b$ | $R^c$ | n |
|---|---|---|---|---|---|
| CH₂ | CH₂ | H | Isopropyl | 2-CH₃ | 1 |
| CH₂ | CH₂ | 2-OH,4-Cl | Hexyl | 2-CH₃ | 1 |
| CH₂ | C(CH₃)₂ | 2,4-Cl | Propyl | 2-CH₃ | 1 |
| CH₂ | CH(CH₃) | 4-CF₃ | sec-Butyl | 3-CH₃ | 1 |
| CH₂ | CH(C₂H₅) | 4-CF₃ | tert-Butyl | 3-CH₃ | 2 |
| CH₂ | CH(Propyl) | 4-CF₃ | Hexyl | 2,6-CH₃ | 3 |
| CH₂ | (CH₂)₂ | 4-CF₃ | Isopropyl | 3-CH₃ | 3 |
| CH₂ | (CH₂)₂ | 4-CF₃ | Cyclopropyl | 3,6-CH₃ | 3 |
| CH₂ | CH₂ | 2-OH,4-CF₃ | Isopropyl | 2-Cl | 1 |
| NH | CH₂ | 4-CF₃ | Isopropyl | H | 1 |

TABLE 29

| X | Y | $R^a$ | $R^b$ | $R^c$ | n |
|---|---|---|---|---|---|
| N(CH₃) | CH₂ | 4-CF₃ | Isopropyl | H | 1 |
| N(CH₃) | CH₂ | 4-CF₃ | Isopropyl | 2-CH₃ | 1 |
| N(C₂H₅) | CH₂ | 4-CF₃ | Isopropyl | H | 1 |
| N(Allyl) | CH₂ | 4-CF₃ | Isopropyl | H | 1 |
| N(Acetyl) | CH₂ | 2-OH,4-Cl | Isopropyl | H | 3 |
| CH₂ | CH₂ | 4-Isopropyl | Isopropyl | 2-CF₃ | 1 |
| CH₂ | CH₂ | 4-CF₃ | Butyl-OCH₂ | 2-CH₃ | 3 |
| NH | CH₂ | 4-CF₃O | CH₃O(CH₂)₅ | 2-CH₃O | 1 |
| N(CH₃) | CH₂ | 4-CF₃ | Hexyl | 2-F | 1 |
| N(CH₃) | (CH₂)₂ | 4-Acetyl | Isopropyl | 2-CH₃ | 2 |

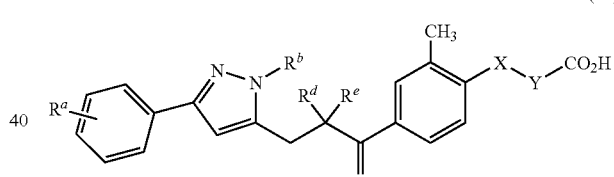

(18)

In the formula, X, Y, $R^a$, $R^b$, $R^d$, $R^e$, and G are set forth in Table 30.

TABLE 30

| X | Y | $R^a$ | $R^b$ | $R^d/R^e$ | G |
|---|---|---|---|---|---|
| CH₂ | CH₂ | 2-OH,4-CF₃ | Isopropyl | H/H | CH₂ |
| CH(CH₃) | CH₂ | 4-CF₃ | Cyclopropylmethyl | H/H | S |
| CH₂ | CH₂ | 4-CF₃ | 4-CF₃-Phenyl | H/H | C(CH₃)₂ |
| CH₂ | CH₂ | 2,4-Cl | CH₃OCH₂CH₂ | CH₃/H | O |
| CH₂ | CH₂ | 4-CH₃ | Heptyl | H/H | CH₂ |
| NH | CH₂ | 4-CF₃ | Isopropyl | H/H | S |
| N(CH₃) | (CH₂)₂ | 4-CF₃ | Isopropyl | H/H | CH₂ |
| CH₂ | CH₂ | 4-CN | Isopropyl | H/H | C(CH₃)₂ |
| CH₂ | CH₂ | 4-t-Butyl | Isopropyl | C₂H₅/H | O |
| CH₂ | (CH₂)₃ | 4-CF₃O | Butyl-OCH₂ | CH₃/H | CH₂ |
| CH₂ | CH₂ | 4-CF₃O | CH₃O(CH₂)₅ | CH₃/CH₃ | O |
| N(CH₃) | CH₂ | 4-t-Butyl | Cyclohexyl | CH₃/CH₃ | O |
| N(C₂H₅) | CH₂ | 4-CF₃ | (CH₃)₂CH(CH₂)₅ | CH₃/CH₃ | O |
| N(Allyl) | CH₂ | 4-CF₃ | 4-CF₃-Benzyl | H/H | S |
| N(Acetyl) | CH₂ | 2,4-CH₃ | Isopropyl | CH₃/CH₃ | CH₂ |

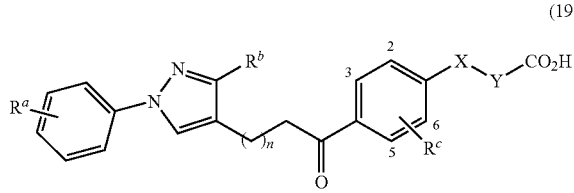

(19)

In the formula, X, Y, $R^a$, $R^b$, $R^c$, and n are set forth in Tables 31 and 32.

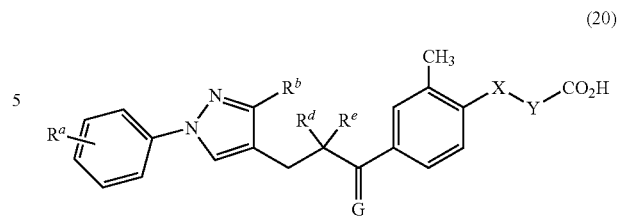

(20)

In the formula, X, Y, $R^a$, $R^b$, $R^d$, $R^e$, and G are set forth in Table 33.

TABLE 33

| X | Y | $R^a$ | $R^b$ | $R^d/R^e$ | G |
|---|---|---|---|---|---|
| $CH_2$ | $CH_2$ | 2-OH,4-$CF_3$ | Isopropyl | H/H | $CH_2$ |
| $CH(CH_3)$ | $CH_2$ | 4-$CF_3$ | Cyclopropylmethyl | H/H | S |
| $CH_2$ | $CH_2$ | 4-$CF_3$ | 4-$CF_3$-Phenyl | H/H | $C(CH_3)_2$ |
| $CH_2$ | $CH_2$ | 2,4-Cl | $CH_3OCH_2CH_2$ | $CH_3$/H | O |
| $CH_2$ | $CH_2$ | 4-$CH_3$ | Heptyl | H/H | $CH_2$ |
| NH | $CH_2$ | 4-$CF_3$ | Isopropyl | H/H | S |
| $N(CH_3)$ | $(CH_2)_2$ | 4-$CF_3$ | Isopropyl | H/H | $CH_2$ |
| $CH_2$ | $CH_2$ | 4-CN | Isopropyl | H/H | $C(CH_3)_2$ |
| $CH_2$ | $CH_2$ | 4-t-Butyl | Isopropyl | $C_2H_5$/H | O |
| $CH_2$ | $(CH_2)_3$ | 4-$CF_3O$ | Butyl-$OCH_2$ | $CH_3/CH_3$ | $CH_2$ |
| $CH_2$ | $CH_2$ | 4-$CF_3O$ | $CH_3O(CH_2)_5$ | $CH_3/CH_3$ | O |
| $N(CH_3)$ | $CH_2$ | 4-t-Butyl | Cyclohexyl | $CH_3/CH_3$ | O |
| $N(C_2H_5)$ | $CH_2$ | 4-$CF_3$ | $(CH_3)_2CH(CH_2)_5$ | $CH_3/CH_3$ | O |
| N(Allyl) | $CH_2$ | 4-$CF_3$ | 4-$CF_3$-Benzyl | H/H | S |
| N(Acetyl) | $CH_2$ | 2,4-$CH_3$ | Isopropyl | $CH_3/CH_3$ | $CH_2$ |

TABLE 31

| X | Y | $R^a$ | $R^b$ | $R^c$ | n |
|---|---|---|---|---|---|
| $CH_2$ | $CH_2$ | 4-$CF_3$ | Isopropyl | 2-$CH_3$ | 1 |
| $CH_2$ | $CH_2$ | 2-OH,4-Cl | Hexyl | 2-$CH_3$ | 1 |
| $CH_2$ | $C(CH_3)_2$ | 2,4-Cl | Propyl | 2-$CH_3$ | 1 |
| $CH_2$ | $CH(CH_3)$ | 4-$CF_3$ | sec-Butyl | 3-$CH_3$ | 1 |
| $CH_2$ | $CH(C_2H_5)$ | 4-$CF_3$ | tert-Butyl | 3-$CH_3$ | 2 |
| $CH_2$ | CH(Propyl) | 4-$CF_3$ | Hexyl | 2,6-$CH_3$ | 3 |
| $CH_2$ | $(CH_2)_2$ | 4-$CF_3$ | Isopropyl | 3-$CH_3$ | 3 |
| $CH_2$ | $(CH_2)_2$ | 4-$CF_3$ | Cyclopropyl | 3,6-$CH_3$ | 3 |
| $CH_2$ | $CH_2$ | 2-OH,4-$CF_3$ | Isopropyl | 2-Cl | 1 |
| NH | $CH_2$ | 4-$CF_3$ | Isopropyl | H | 1 |

TABLE 32

| X | Y | $R^a$ | $R^b$ | $R^c$ | n |
|---|---|---|---|---|---|
| $N(CH_3)$ | $CH_2$ | 4-$CF_3$ | Isopropyl | H | 1 |
| $N(CH_3)$ | $CH_2$ | 4-$CF_3$ | Isopropyl | 2-$CH_3$ | 1 |
| $N(C_2H_5)$ | $CH_2$ | 4-$CF_3$ | Isopropyl | H | 1 |
| N(Allyl) | $CH_2$ | 4-$CF_3$ | Isopropyl | H | 1 |
| N(Acetyl) | $CH_2$ | 2-OH,4-Cl | Isopropyl | H | 3 |
| $CH_2$ | $CH_2$ | 4-Isopropyl | Isopropyl | 2-$CF_3$ | 1 |
| $CH_2$ | $CH_2$ | 4-$CF_3$ | Butyl-$OCH_2$ | 2-$CH_3$ | 3 |
| NH | $CH_2$ | 4-$CF_3O$ | $CH_3O(CH_2)_5$ | 2-$CH_3O$ | 1 |
| $N(CH_3)$ | $CH_2$ | 4-$CF_3$ | Hexyl | 2-F | 1 |
| $N(CH_3)$ | $(CH_2)_2$ | 4-Acetyl | Isopropyl | 2-$CH_3$ | 2 |

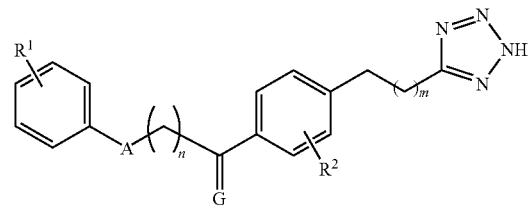

(21)

In the formula, A, $R^1$, $R^2$, m, n, and G are set forth in Tables 34 and 35.

TABLE 34

| A | $R^1$ | $R^2$ | m | n | G |
|---|---|---|---|---|---|
| 2,5-dimethylthiazol-4-yl (Pr at 4) | 4-$CF_3$ | 2-$CH_3$ | 2 | 1 | O |
| 2,5-dimethylthiophen-3-yl (Pr at 3) | 4-$CF_3$ | 2-$CH_3$ | 2 | 1 | O |
| 2,5-dimethylfuran-3-yl (Pr at 3) | 4-$CF_3$ | 2-$CH_3$ | 3 | 1 | $CH_2$ |

TABLE 34-continued

| A | R¹ | R² | m | n | G |
|---|---|---|---|---|---|
| 2,5-dimethyl-4-Pr-oxazol-4-yl | 4-CF₃ | 2-CH₃ | 2 | 1 | O |
| 2,4-dimethyl-5-Pr-oxazol-5-yl | 2-OH, 4-Cl | 3-CH₃ | 2 | 1 | O |
| 1,4-dimethyl-3-Pr-pyrazol-3-yl | 4-CF₃ | 3-CH₃ | 2 | 2 | O |
| 3,5-dimethyl-1-Pr-pyrazol-1-yl | 4-CF₃ | 2,6-CH₃ | 2 | 3 | O |

TABLE 35

| A | R¹ | R² | m | n | G |
|---|---|---|---|---|---|
| 2,5-dimethyl-4-cyclopropyl-thiazol-4-yl | 4-CF₃ | 2-CH₃ | 3 | 1 | O |
| 2,5-dimethyl-3-Pr-thiophen-3-yl | 4-CF₃ | 2-CH₃ | 2 | 1 | O |
| 2-methyl-5-t-butyl-thiophen-3-yl | 4-CF₃ | 2-CH₃ | 2 | 1 | CH₂ |
| 2,5-dimethyl-4-sec-butyl-oxazol-4-yl | 2-OH, 4-Cl | 3-CH₃ | 3 | 1 | O |
| 2,4-dimethyl-5-isopropyl-oxazol-5-yl | 4-CH₃ | 3-CH₃ | 1 | 1 | O |
| 1-methyl-4-(2-methoxyethyl)-pyrazol-4-yl | 4-CF₃ | 3-CH₃ | 2 | 2 | O |

TABLE 35-continued

| A | R¹ | R² | m | n | G |
|---|---|---|---|---|---|
| 3,5-dimethyl-1-isopropyl-pyrazol-1-yl | 4-CF₃ | 2,6-CH₃ | 2 | 3 | O |

$$\text{(22)}$$

R¹—(phenyl)—A—(CH=CN)ₙ—C(=G)—(phenyl-R²)—CH=CH—CO₂H

In the formula, A, R¹, R², n, and G are set forth in Tables 36 and 37.

TABLE 36

| A | R¹ | R² | n | G |
|---|---|---|---|---|
| 2,5-dimethyl-4-isopropyl-thiazol-4-yl | 4-CF₃ | 2-CH₃ | 1 | O |
| 2,5-dimethyl-3-isopropyl-thiophen-3-yl | 4-CF₃ | 2-CH₃ | 1 | O |
| 2,5-dimethyl-3-isopropyl-furan-3-yl | 4-CF₃ | 2-CH₃ | 2 | CH₂ |
| 2,5-dimethyl-4-isopropyl-oxazol-4-yl | 4-CF₃ | 2-CH₃ | 2 | O |
| 2,4-dimethyl-5-isopropyl-oxazol-5-yl | 2-OH, 4-Cl | 3-CH₃ | 2 | O |
| 1,4-dimethyl-3-isopropyl-pyrazol-3-yl | 4-CF₃ | 3-CH₃ | 2 | O |
| 3,5-dimethyl-1-isopropyl-pyrazol-1-yl | 4-CF₃ | 2,6-CH₃ | 2 | O |

TABLE 37

| A | R$^1$ | R$^2$ | n | G |
|---|---|---|---|---|
| cyclopropyl (2,5-dimethylthiazol-4-yl) | 4-CF$_3$ | 2-CH$_3$ | 3 | O |
| Pr (2,5-dimethylthiophen-3-yl) | 4-CF$_3$ | 2-CH$_3$ | 2 | O |
| t-butyl (2,5-dimethylthiophen-3-yl) | 4-CF$_3$ | 2-CH$_3$ | 2 | CH$_2$ |
| sec-butyl (2,5-dimethyloxazol-4-yl) | 2-OH, 4-Cl | 3-CH$_3$ | 3 | O |
| isopropyl (2,4-dimethyloxazol-5-yl) | 4-CH$_3$ | 3-CH$_3$ | 1 | O |
| 2-methoxyethyl (1,4-dimethylpyrazol-3-yl) | 4-CF$_3$ | 3-CH$_3$ | 2 | O |
| isopropenyl (1,3-dimethylpyrazol-5-yl) | 4-CF$_3$ | 2,6-CH$_3$ | 2 | O |

The pharmacological effects of the invention are described below.

The PPAR activating effect of the compound of the invention was determined by the following method:

A receptor expression plasmid (pSG5-GAL4-hPPARα or γ or δ (LBD)), a luciferase expression plasmid (MH100×4-TK-Luc), and a β-galactosidase expression plasmid (pCMX-β-GAL) are transfected into CV-1 cells (ATCC) (Kliewer, S. A. et al., (1992) Nature, 358: 771-774). After the gene transfer is conducted by utilizing a lipofection reagent (Lipofectamine 2000, Invitrogen), it is incubated for about 40 hours in the presence of a compound to be tested. The luciferase activity and β-GAL activity are measured on the soluble cells.

The luciferase activity is calibrated by the β-GAL activity. A relative ligand activity is calculated under the condition that the luciferase activity of the cells treated by GW-590735 for PPARα, Rosiglitazone for PPARγ, or GW-501516 for PPARδ is set to 100% to determine EC$_{50}$ (see the below-mentioned Examples 14 and 15).

In contrast to the description of Bioorg Med Chem Lett 13 (2003) 1517-1521 that the activating function of phenylpropionic acid type for PPARδ is weak, the compounds of the invention show an excellent activating effect for transcription of PPARδ, as is shown in Tables 38 and 39. As is described above, the compounds represented by the formula (I), (II), and (III) are strong PPARδ agonists.

A medicament of the PPARδ agonist of the present invention is effective for treatment or prophylaxis of diseases mediated by PPARδ. The diseases include hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity including internal-organs fat type, diabetes, hyperglycemia, insulin resistance, impaired glucose tolerance, hyperinsulinism, diabetic complication, cardiac insufficiency, cardiac infarction, cardiomyopathy, hypertension, fatty liver, non-alcoholic fatty hepatitis, thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, pancreatitis, or cancer including colon cancer, large intestine cancer, skin cancer, cancer of the breast, carcinoma of the prostate, ovary cancer, and lung cancer.

The compound of the invention can be administered to human beings by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

For the preparation of these pharmaceuticals, ordinary additives such as vehicles, disintegrators, binders, lubricants, dyes, and diluents can be used. As the vehicles, lactose, D-mannitol, crystalline cellulose and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpyrrolidone (PVP) as the binders.

The compound of the invention can be administered to an adult generally in an amount of 0.1 mg to 100 mg a day by parenteral administration and 1 mg to 2,000 mg a day by oral administration. The dosage can be adjusted in consideration of age and conditions of the patient.

The invention is further described by the following non-limiting examples.

EXAMPLES

Example 1

3-[4-[3-[4-Hexyl-2-(4-methylphenyl)thiazol-5-yl]propionyl]-2-methylphenyl]propionic acid (1) 4-Hexyl-2-(4-methylphenyl)thiazole-5-carboaldehyde [4-Hexyl-2-(4-methylphenyl)thiazol-5-yl]methanol (500 mg, 1.727 mmol) was dissolved in anhydrous methylene chloride (6 mL). Molecular sieve (3A powder, 890 mg) and pyridinium chlorochromate (745 mg, 3.455 mmol) were added to the solution. The mixture was stirred at room temperature for 30 minutes. Diethyl ether (20 mL) and Silica gel (Wako-gel, C-300HG, 2 g) were added to the mixture. The resulting mixture was further stirred at room temperature for 10 minutes. The reaction mixture was filtrated through glass filter. The residue was washed with diethyl ether. The solvent was removed from the obtained filtrate under reduced pressure. The obtained residue was purified by silica gel column chromatography with hexane/ethyl:acetate (8:1, v/v) to give the desired compound (346 mg) as white crystalline product (yield 70%).

$^1$H NMR (CDCl$_3$, 400 MHz): δ=0.89 (3H, t, J=7 Hz), 1.3-1.4 (6H, m), 1.8-1.9 (2H, m), 2.41 (3H, s), 3.09 (2H, t, J=7 Hz), 7.27 (2H, d, J=8 Hz), 7.90 (2H, d, J=8 Hz), 10.08 (1H, s).

(2) Methyl 3-(4-acetyl-2-methylphenyl)-2-bromopropionate 1-(4-Amino-3-methylphenyl)ethanone (1.70 g, 11.39 mmol) was dissolved in methanol (15 mL)-acetone (38 mL). The solution was cooled to 0° C. 48% Hydrobromic acid (5.15 mL, 45.56 mmol) was dropwise added to the solution for 1 minute. A solution of sodium nitrite (943 mg, 13.67 mmol) in water (1.8 mL) was further added to the solution. The mixture was stirred at the same temperature for 30 minutes. The mixture was left to room temperature. Methyl acrylate (7.23 mL, 80.30 mmol) and copper(I) oxide (117 mg) were added to the mixture. The resulting mixture was stirred at 40° C. for 30 minutes. The solvent was removed under reduced pressure. Ice-cold water (150 mL) was added to the residue. The mixture was neutralized with ammonia water, and extracted with ethyl acetate. The organic layer was washed with saturated brine, and dried with anhydrous sodium sulfate. The solvent was removed under reduced pressure to give the desired compound (2.79 g) as brown oil (yield 82%).

$^1$H NMR (CDCl$_3$, 400 MHz): δ=2.41 (3H, s), 2.58 (3H, s), 3.33 (1H, dd, J=7, 15 Hz), 3.52 (1H, dd, J=7, 15 Hz), 3.74 (3H, s), 4.43 (1H, t, J=7 Hz), 7.2-7.9 (3H, m).

(3) 3-(4-Acetyl-2-methylphenyl)acrylic acid

The obtained methyl 3-(4-acetyl-2-methylphenyl)-2-bromopropionate (2.79 g, 9.33 mmol) was dissolved in methanol (80 mL). The solution was cooled to 5° C. Sodium methoxide (1.51 g, 27.98 mmol) was added to the solution. The mixture was stirred at room temperature for 20 minutes, refluxed for 1 hour, cooled to room temperature, and acidized with 1N hydrochloric acid. Water (50 mL) was added to the mixture. The mixture was extracted with chloroform. The organic layer was dried with anhydrous sodium sulfate. The solvent was removed under reduced pressure to give 657 mg of the desired compound as yellow crystalline product (yield 34%).

$^1$H NMR (CD$_3$OD, 400 MHz): δ=2.49 (3H, s), 2.59 (3H, s), 6.49 (1H, d, J=16 Hz), 7.73 (1H, d, J=8 Hz), 7.8-7.9 (3H, m), 7.97 (1H, d, J=16 Hz).

(4) Methyl 3-(4-acetyl-2-methylphenyl)acrylate

The obtained 3-(4-acetyl-2-methylphenyl)acrylic acid (657 mg, 3.22 mmol) was dissolved in methanol (20 mL). Concentrated sulfuric acid (250 µL) was added to the solution. The mixture was refluxed for 2 hours, and cooled to room temperature. Water (50 mL) was added to the solution. Methanol was removed under reduced pressure. The solution was extracted with ethyl acetate, washed with saturated aqueous sodium bicarbonate solution and saturated brine. The organic layer was dried with anhydrous sodium sulfate. The solvent was removed under reduced pressure. The obtained residue was purified by silica gel column chromatography with hexane/ethyl acetate (9:1, v/v) to give the desired compound (665 mg) as yellow crystalline product (yield 95%).

$^1$H NMR (CDCl$_3$, 400 MHz): δ=2.49 (3H, s), 2.60 (3H, s), 3.83 (3H, s), 6.43 (1H, d, J=16 Hz), 7.62 (1H, d, J=9 Hz), 7.7-7.8 (2H, m), 7.96 (1H, d, J=16 Hz).

(5) Methyl 3-[4-[3-[4-hexyl-2-(4-methylphenyl)thiazol-5-yl]propenoyl]-2-methylphenyl]acrylate The obtained methyl 3-(4-acetyl-2-methylphenyl)acrylate (200 mg, 0.916 mmol) was dissolved in anhydrous tetrahydrofuran (1 mL) under nitrogen atmosphere. Molecular sieve (3A powder, 200 mg) was added to the solution. 0.5 M solution of sodium methoxide in methanol (1.83 mL, 0.916 mmol) was added to the solution cooled with ice while stirring. The mixture was stirred at the same temperature for 10 minutes. A solution (1 mL) of 4-hexyl-2-(4-methylphenyl)thiazole-5-carboaldehyde obtained at (1) of Example 1 (132 mg, 0.458 mmol) in anhydrous tetrahydrofuran was slowly added to the mixture. The resulting mixture was stirred while cooling with ice for 3 hours. The organic layer was dried with anhydrous sodium sulfate. The solvent was removed under reduced pressure. The residue was recrystallized with hexane and ethyl acetate to give the desired compound (185 mg) as yellow crystalline product (yield 83%).

$^1$H NMR (CDCl$_3$, 400 MHz): δ=0.89 (3H, t, J=7 Hz), 1.3-1.5 (6H, m), 1.7-1.8 (2H, m), 2.41 (3H, s), 2.53 (3H, s), 2.93 (2H, t, J=7 Hz), 3.84 (3H, s), 6.46 (1H, d, J=16 Hz), 7.20 (1H, d, J=16 Hz), 7.8-7.9 (2H, m), 7.66 (1H, d, J=8 Hz), 7.8-7.9 (4H, m), 7.99 (1H, d, J=16 Hz), 8.02 (1H, d, J=16 Hz).

(6) Methyl 3-[4-[3-[4-hexyl-2-(4-methylphenyl)thiazol-5-yl]propionyl]-2-methylphenyl]propionate The obtained methyl 3-[4-[3-[4-hexyl-2-(4-methylphenyl)thiazol-5-yl]propenoyl]-2-methylphenyl]acrylate (112 mg, 0.230 mmol) was dissolved in methanol (1 mL) and tetrahydrofuran (1 mL). 10% palladium carbon (22 mg) was added to the solution to cause replacement of hydrogen in the system. The mixture was stirred at room temperature for 3 hours. The reaction mixture was filtrated with Celite. The filtrate was concentrated under reduced pressure. The obtained residue was purified by silica gel column chromatography with hexane/ethyl acetate (5:1, v/v) to give the desired compound (46 mg) as colorless oil (yield 41%).

$^1$H NMR (CDCl$_3$, 400 MHz): δ=0.88 (3H, t, J=7 Hz), 1.2-1.4 (6H, m), 1.6-1.8 (2H, m), 2.37 (3H, s), 2.38 (3H, s), 2.61 (2H, t, J=8 Hz), 2.72 (2H, t, J=8 Hz), 2.99 (2H, t, J=8 Hz), 3.2-3.3 (4H, m), 3.68 (3H, s), 7.19 (2H, d, J=8 Hz), 7.23 (1H, d, J=8 Hz), 7.7-7.8 (4H, m).

(7) 3-[4-[3-[4-Hexyl-2-(4-methylphenyl)thiazol-5-yl]propionyl]-2-methylphenyl]propionic acid The obtained methyl 3-[4-[3-[4-hexyl-2-(4-methylphenyl)thiazol-5-yl]propionyl]-2-methylphenyl]propionate (45 mg, 0.0915 mmol) was suspended in ethanol (2 mL) and water (1 mL). Lithium hydroxide monohydrate (12 mg, 0.275 mmol) was added to the suspension. The mixture was refluxed for 1 hour. 1N hydrochloric acid (5 mL) and ice-cooled water (2 mL) were added to the mixture. The mixture was extracted with ethyl acetate. The organic layer was washed with brine, and dried with anhydrous sodium sulfate. The solvent was removed under reduced pressure. The obtained residue was recrystallized with hexane and ethyl acetate to give the desired compound (38 mg) as while crystalline product (yield 87%).

FAB-MS (m/e): 478 (M+1), $^1$H NMR (CDCl$_3$, 400 MHz): δ=0.88 (3H, t, J=7 Hz), 1.3-1.4 (6H, m), 1.6-1.8 (2H, m), 2.37 (3H, s), 2.38 (3H, s), 2.6-2.8 (4H, m), 3.00 (2H, t, J=8 Hz), 3.1-3.3 (4H, m), 7.19 (2H, d, J=8 Hz), 7.24 (1H, s), 7.7-7.8 (4H, m).

Example 2

3-[4-[3-[3-Isopropyl-5-[4-(trifluoromethyl)phenyl]thiophen-2-yl]propionyl]-2-methylphenyl]propionic acid (1) 3-Isopropyl-5-[4-(trifluoromethyl)phenyl]thiophene-2-carboaldehyde The subject compound was obtained in an analogous manner to (1) of Example 1 from [3-Isopropyl-5-[4-(trifluoromethyl)phenyl]thiophen-2-yl]methanol.
Pale Yellow Crystalline Product
Yield 57% $^1$H NMR (CDCl$_3$, 400 MHz): δ=1.39 (6H, d, J=7 Hz), 3.6-3.8 (1H, m), 7.37 (1H, s), 7.68 (2H, d, J=8 Hz), 7.77 (2H, d, J=8 Hz), 10.11 (1H, s).

(2) Methyl 3-[4-[3-[3-isopropyl-5-[4-(trifluoromethyl)phenyl]thiophene-2-yl]propenoyl]-2-methylphenyl]acrylate The subject compound was obtained in an analogous manner to (5) of Example 1.
Yellow Crystalline Product
Yield 67%
$^1$H NMR (CDCl$_3$, 400 MHz): δ=1.32 (6H, d, J=7 Hz), 2.54 (3H, s), 3.3-3.5 (1H, m), 3.84 (3H, s), 6.46 (1H, d, J=16 Hz), 7.3-7.4 (1H, m), 7.6-7.9 (8H, m), 8.00 (1H, d, J=15 Hz), 8.11 (1H, d, J=15 Hz).

(3) Methyl 3-[4-[3-[3-isopropyl-5-[4-(trifluoromethyl)phenyl]thiophene-2-yl]propionyl]-2-methylphenyl]propionate The subject compound was obtained in an analogous manner to (6) of Example 1.
Pale Yellow Crystalline Product
Yield 58%
$^1$H NMR (CDCl$_3$, 400 MHz): δ=1.26 (6H, d, J=7 Hz), 2.38 (3H, s), 2.61 (2H, t, J=8 Hz), 2.99 (2H, t, J=8 Hz), 3.0-3.1 (1H, m), 3.2-3.4 (4H, m), 3.68 (3H, s), 7.20 (1H, s), 7.23 (1H, d, J=8 Hz), 7.58 (2H, d, J=8 Hz), 7.64 (2H, d, J=8 Hz), 7.7-7.8 (2H, m).

(4) 3-[4-[3-[3-Isopropyl-5-[4-(trifluoromethyl)phenyl]thiophene-2-yl]propionyl]-2-methylphenyl]propionic acid The subject compound was obtained in an analogous manner to (7) of Example 1.
White Crystalline Product
Yield 79%
FAB-MS (m/e): 488 (M),
$^1$H NMR (CDCl$_3$, 400 MHz): δ=1.25 (6H, d, J=7 Hz), 2.38 (3H, s), 2.67 (2H, t, J=8 Hz), 3.01 (2H, t, J=8 Hz), 3.0-3.1 (1H, m), 3.2-3.4 (4H, m), 7.20 (1H, s), 7.24 (1H, s), 7.58 (2H, d, J=8 Hz), 7.64 (2H, d, J=8 Hz), 7.7-7.8 (1H, m), 7.77 (1H, s).

Example 3

3-[4-[3-(5-Isopropyl-2-phenyl-4-oxazolyl)propionyl]-2-methylphenyl]propionic acid (1) 5-Isopropyl-2-(2,4-dichlorophenyl)oxazole-4-carboaldehyde The subject compound was obtained in an analogous manner to (1) of Example 1 from 5-isopropyl-2-(2,4-dichlorophenyl)oxazole-4-methanol.
Pale Yellow Crystalline Product
$^1$H NMR (CDCl$_3$, 400 MHz): δ=1.39 (6H, d, J=7 Hz), 3.72 (1H, dq, J=7, 7 Hz), 7.37 (1H, dd, J=2, 8 Hz), 7.55 (1H, d, J=2 Hz), 7.99 (1H, d, J=8 Hz), 10.06 (1H, s).

(2) Methyl 3-[4-[3-[5-isopropyl-2-(2,4-dichlorophenyl)-4-oxazolyl]propenoyl]-2-methylphenyl]acrylate The subject compound was obtained in an analogous manner to (5) of Example 1 from the obtained 5-isopropyl-2-(2,4-dichlorophenyl)oxazole-4-carboaldehyde and methyl 3-(4-acetyl-2-methylphenyl)acrylate.
Pale Yellow Crystalline Product
$^1$H NMR (CDCl$_3$, 400 MHz): δ=1.39 (6H, d, J=7 Hz), 2.52 (3H, s), 3.39 (1H, dq, J=7, 7 Hz), 3.83 (3H, s), 6.46 (1H, d, J=16 Hz), 7.38 (1H, dd, J=2, 8 Hz), 7.55 (1H, d, J=2 Hz), 7.66 (1H, d, J=8 Hz), 7.75 (1H, d, J=15 Hz), 7.80 (1H, d, J=15 Hz), 7.9-8.0 (2H, m), 7.99 (1H, d, J=16 Hz), 8.01 (1H, d, J=8 Hz).

(3) Methyl 3-[4-[3-(5-isopropyl-2-phenyl-4-oxazolyl)propionyl]-2-methylphenyl]propionate The subject compound was obtained in an analogous manner to (6) of Example 1 from the methyl 3-[4-[3-[5-isopropyl-2-(2,4-dichlorophenyl)-4-oxazolyl]propenoyl]-2-methylphenyl]acrylate.
Colorless Oil
$^1$H NMR (CDCl$_3$, 400 MHz): δ=1.30 (6H, d, J=7 Hz), 2.35 (3H, s), 2.59 (2H, t, J=7 Hz), 2.9-3.1 (4H, m), 3.17 (1H, dq, J=7, 7 Hz), 3.36 (2H, t, J=7 Hz), 3.67 (3H, s), 7.20 (1H, d, J=8 Hz), 7.3-7.5 (3H, m), 7.7-7.9 (2H, m), 7.9-8.1 (2H, m).

(4) 3-[4-[3-(5-Isopropyl-2-phenyl-4-oxazolyl)propionyl]-2-methylphenyl]propionic acid The subject compound was obtained in an analogous manner to (7) of Example 1 from the methyl 3-[4-[3-(5-isopropyl-2-phenyl-4-oxazolyl)propionyl]-2-methylphenyl]propionate.
Colorless Oil
FAB-MS (m/e): 406 (M+1) $^1$H NMR (CDCl$_3$, 400 MHz): δ=1.30 (6H, d, J=7 Hz), 2.35 (3H, s), 2.63 (2H, t, J=7 Hz), 2.9-3.1 (4H, m), 3.17 (1H, dq, J=7, 7 Hz), 3.34 (2H, t, J=7 Hz), 7.21 (1H, d, J=8 Hz), 7.3-7.5 (3H, m), 7.7-7.9 (2H, m), 7.9-8.1 (2H, m).

Example 4

3-[4-[3-[4-Isopropyl-2-[4-(trifluoromethyl)phenyl]thiazol-5-yl-]propenoyl]-2-methylphenyl]acrylic acid The desired compound was obtained in an analogous manner to (5) of Example 1 from methyl 3-(4-acetyl-2-methylphenyl)acrylate and [4-isopropyl-2-[4-(trifluoromethyl)phenyl]thiazol-5-yl]carboaldehyde.
Yellow Crystalline Product
FAB-MS (m/e): 486 (M+1)
$^1$H NMR (CDCl$_3$, 400 MHz): δ=1.40 (6H, d, J=7 Hz), 2.56 (3H, s), 3.4-3.5 (1H, m), 6.49 (1H, d, J=16 Hz), 7.28 (1H, d, J=16 Hz), 7.7-7.8 (3H, m), 7.8-7.9 (2H, m), 8.0-8.2 (4H, m).

Example 5

3-[4-[3-[4-Isopropyl-2-[4-(trifluoromethyl)phenyl]thiazol-5-yl]propionyl]-2-methylphenyl]propionic acid The desired compound was obtained in an analogous manner as in (6) of Example 1 using the 3-[4-[3-[4-Isopropyl-2-

[4-(trifluoromethyl)phenyl]thiazol-5-yl-]propenoyl]-2-methylphenyl]acrylic acid prepared in Example 4.

White Crystalline Product

FAB-MS (m/e): 490 (M+1)

$^1$H NMR (CDCl$_3$, 400 MHz): δ=1.33 (6H, d, J=7 Hz), 2.38 (3H, s), 2.66 (2H, t, J=8 Hz), 3.00 (2H, t, J=8 Hz), 3.1-3.2 (1H, m), 3.2-3.3 (4H, m), 7.25 (1H, d, J=7 Hz), 7.64 (2H, d, J=8 Hz), 7.7-7.8 (2H, m), 8.00 (2H, d, J=8 Hz).

Example 6

3-[4-[1-[2-[4-Isopropyl-2-[4-(trifluoromethyl)phenyl]thiazol-5-yl]ethyl]vinyl]-2-methylphenyl]propionic acid (1) Methyl 3-[4-[1-[2-[4-isopropyl-2-[4-(trifluoromethyl)phenyl]thiazol-5-yl]ethyl]vinyl]-2-methylphenyl]propionate Methyltriphenylphosphonium bromide (89 mg, 0.250 mmol) was suspended in anhydrous tetrahydrofuran (3.5 mL) under nitrogen atmosphere. The suspension was stirred at room temperature for 30 minutes. A solution (1.5 mL) of methyl 3-[4-[3-[4-isopropyl-2-[4-(trifluoromethyl)phenyl]thiazol-5-yl]propionyl]2-methylphenyl]propionate (84 mg, 0.167 mmol) in anhydrous tetrahydrofuran was dropwise added to the suspension. The mixture was stirred at the same temperature for 19 hours. A saturated aqueous ammonium chloride solution was drop-wise added to the mixture. The mixture was extracted with ethyl acetate. The organic layer was washed with saturated brine, and dried with anhydrous sodium sulfate. The solvent was removed under reduced pressure.

The obtained residue was purified by silica gel column chromatography with hexane/ethyl acetate (8:1, v/v) to give the desired compound (70 mg) as pale yellow oil (yield 84%).

$^1$H NMR (CDCl$_3$, 400 MHz): δ=1.28 (6H, d, J=7 Hz), 2.34 (3H, s), 2.5-2.7 (2H, m), 2.8-2.9 (2H, m), 2.9-3.1 (5H, m), 3.69 (3H, s), 5.06 (1H, s), 5.31 (1H, s), 7.13 (1H, d, J=9 Hz), 7.1-7.3 (2H, m), 7.64 (2H, d, J=8 Hz), 8.01 (2H, d, J=8 Hz).

(2) 3-[4-[1-[2-[4-Isopropyl-2-[4-(trifluoromethyl)phenyl]thiazol-5-yl]ethyl]vinyl]-2-methylphenyl]propionic acid The desired compound was obtained in an analogous manner as in (7) of Example 1.

White Crystalline Product

FAB-MS (m/e): 488 (M+1)

$^1$H NMR (CDCl$_3$, 400 MHz): δ=1.28 (6H, d, J=7 Hz), 2.35 (3H, s), 2.66 (2H, dd, J=7, 8 Hz) 2.82 (2H, dd, J=7, 8 Hz), 2.9-3.0 (5H, m), 5.07 (1H, s), 5.32 (1H, s), 7.1-7.3 (3H, m), 7.64 (2H, d, J=8 Hz), 8.00 (2H, d, J=8 Hz).

Example 7

N-[4-[3-[4-Isopropyl-2-[4-(trifluoromethyl)phenyl]thiazol-5-yl]propionyl]phenyl]-N-methylglycine (1) 3-[4-Isopropyl-2-[4-(trifluoromethyl)phenyl]thiazol-5-yl]-1-(4-nitrophenyl)propenone 4-Isopropyl-2-[4-(trifluoromethyl)phenyl]thiazole-5-carboaldehyde (4.53 g, 15.14 mmol) and 4-nitroacetophenone (2.50 g, 15.14 mmol) were dissolved in a mixture of anhydrous methanol (30 mL) and anhydrous tetrahydrofuran (30 mL). Sodium methoxide (258 mg, 3.79 mmol) was added to the solution. The resulting mixture was stirred at room temperature for 1 hour under nitrogen atmosphere. The solvent was removed under reduced pressure. The mixture was suspended in chloroform. Insoluble matters were filtered, washed with water, a saturated aqueous sodium bicarbonate solution, and saturated brine. The solvent was again removed under reduced pressure. The residue was recrystallized with n-hexane and ethyl acetate (1:1) to give the desired compound (4.08 g) as yellow crystalline produce (yield 60%).

$^1$H NMR (CDCl$_3$, 400 MHz): δ=1.40 (6H, d, J=7 Hz), 3.4-3.5 (1H, m), 7.24 (1H, d, J=12 Hz), 7.73 (2H, d, J=8 Hz), 8.14 (5H, m), 8.37 (2H, d, J=8 Hz).

(2) 1-(4-Aminophenyl)-3-[4-isopropyl-2-[4-(trifluoromethyl)phenyl]thiazol-5-yl]-propan-1-one The obtained 3-[4-isopropyl-2-[4-(trifluoromethyl)phenyl]thiazol-5-yl]-1-(4-nitrophenyl)propenone (4.08 g, 9.14 mmol) was dissolved in tetrahydrofuran (120 mL) and methanol (100 mL). 10% suspension (20 mL) of palladium carbon (400 mg) was added to the solution. The mixture was stirred at 60° C. for 2 hours under atmosphere of hydrogen. The mixture was cooled to room temperature. Insoluble matters were filtered. The solvent was removed under reduced pressure. The residue was purified by silica gel column chromatography with hexane/ethyl acetate (7:3, v/v) to give the desired compound (2.31 g) as yellow crystalline product (yield 60%).

$^1$H NMR (CDCl$_3$, 400 MHz): δ=1.33 (6H, d, J=7 Hz), 3.1-3.3 (5H, m), 4.12 (2H, br s), 6.65 (2H, td, J=2, 8 Hz), 7.63 (2H, d, J=8 Hz), 7.82 (2H, td, J=2, 8 Hz), 8.00 (2H, d, J=8 Hz).

(3) N-[4-[3-[4-Isopropyl-2-[4-(trifluoromethyl)phenyl]thiazol-5-yl]propionyl]phenyl]-2-nitrobenzenesulfonamide The obtained 1-(4-aminophenyl)-3-[4-isopropyl-2-[4-(trifluoromethyl)phenyl]thiazol-5-yl]-propan-1-one (250 mg, 0.597 mmol) was dissolved in anhydrous pyridine (5 mL). O-nitrophenylsulfonyl chloride (146 mg, 0.659 mmol) was added to the solution. The mixture was stirred at room temperature for 1 hour. The outer temperature was heated to 80° C., and the mixture was further stirred for 16 hours. The mixture was cooled to room temperature. Water was added to the mixture. The mixture was extracted with ethyl acetate. The organic layer was washed with a saturated aqueous sodium bicarbonate solution and saturated brine, and dried with anhydrous sodium sulfate to remove the solvent. The obtained residue was purified by silica gel column chromatography with hexane/ethyl acetate (8:2, v/v) to give the desired compound (265 mg) as yellow crystalline product (yield 74%).

$^1$H NMR (CDCl$_3$, 400 MHz): δ=1.32 (6H, d, J=7 Hz), 3.0-3.2 (1H, m), 3.2-3.3 (4H, m), 7.32 (2H, d, J=8 Hz), 7.45 (1H, s), 7.6-7.7 (4H, m), 7.87 (1H, d, J=8 Hz), 7.90 (2H, d, J=8 Hz), 7.94 (1H, dd, J=1, 8 Hz), 7.99 (2H, d, J=8 Hz).

(4) N-[4-[3-[4-Isopropyl-2-[4-(trifluoromethyl)phenyl]thiazol-5-yl]propionyl]phenyl]-N-methyl-2-nitrobenzenesulfonamide The obtained N-[4-[3-[4-isopropyl-2-[4-(trifluoromethyl)phenyl]thiazol-5-yl]propionyl]phenyl]-2-nitrobenzenesulfonamide (265 mg, 0.439 mmol) was dissolved in anhydrous dimethylformamide (10 mL). Iodomethane (30 μL, 0.483 mmol) and potassium carbonate (121 mg, 0.875 mmol) were added to the solution. The mixture was stirred at room temperature for 16 hours. The mixture was neutralized with 0.2 N aqueous solution of hydrochloric acid, and extracted with ethyl acetate. The organic layer was washed with a saturated aqueous sodium bicarbonate solution and saturated brine, and dried with anhydrous sodium sulfate to remove the solvent. The obtained residue was purified by silica gel column chromatography with hexane/ethyl acetate (7:3, v/v) to give the desired compound (230 mg) as yellow oil (yield 85%).

$^1$H NMR (CDCl$_3$, 400 MHz): δ=1.34 (6H, d, J=7 Hz), 3.1-3.2 (1H, m), 3.2-3.4 (4H, m), 3.41 (3H, s), 7.38 (2H, d, J=8 Hz), 7.5-7.8 (6H, m), 7.94 (2H, d, J=8 Hz), 8.00 (2H, d, J=8 Hz).

(5) 3-[4-Isopropyl-2-[4-(trifluoromethyl)phenyl]thiazol-5-yl]-1-(4-methylaminophenyl)propan-1-one The obtained N-[4-[3-[4-isopropyl-2-[4-(trifluoromethyl)phenyl]thiazol-5-yl]propionyl]phenyl]-N-methyl-2-nitrobenzenesulfonamide (230 mg, 0.372 mmol) was dissolved in anhydrous dimethylformamide (5 mL). Potassium carbonate (154 mg, 1.116 mmol) and thiophenol (46 μL, 0.446 mmol) were added to the solution. The mixture was stirred at room temperature for 1 hour. The mixture was diluted with water, and extracted with ethyl acetate. The organic layer was washed with water, a saturated aqueous sodium bicarbonate solution, and saturated brine, and dried with anhydrous sodium sulfate. The solvent was removed under reduced pressure. The obtained residue was purified by silica gel column chromatography with hexane/ethyl acetate (8:2, v/v) to give the desired compound (154 mg) as yellow crystalline product (yield 95%).

$^1$H NMR (CDCl$_3$, 400 MHz): δ=1.33 (6H, d, J=7 Hz), 2.90 (3H, d, J=5 Hz), 3.1-3.3 (5H, m), 4.26 (1H, br s), 6.56 (2H, d, J=8 Hz), 7.63 (2H, d, J=8 Hz), 7.85 (2H, d, J=8 Hz), 8.00 (2H, d, J=8 Hz).

(6) Ethyl ester of N-[4-[3-[4-isopropyl-2-[4-(trifluoromethyl)phenyl]thiazol-5-yl]propionyl]phenyl]-N-methylglycine The obtained 3-[4-Isopropyl-2-[4-(trifluoromethyl)phenyl]thiazol-5-yl]-1-(4-methylaminophenyl)propan-1-one (40 mg, 0.0931 mmol) and diisopropylethylamine (80 μL, 0.462 mmol) were dissolved in anhydrous dimethylformamide (2 mL). Ethyl bromoacetate (66 mg, 0.393 mmol) was added to the solution. The mixture was stirred at 110° C. for 16 hours. The mixture was cooled to room temperature, diluted with water, and extracted with ethyl acetate. The organic layer was washed with saturated brine, and dried with anhydrous sodium sulfate to remove the solvent. The obtained residue was purified by silica gel column chromatography with hexane/chloroform (7:3, v/v) to give the desired compound (56 mg) as yellow crystalline product (yield 47%).

$^1$H NMR (CDCl$_3$, 400 MHz): δ=1.25 (3H, t, J=7 Hz), 1.33 (6H, d, J=7 Hz), 3.14 (3H, s), 3.1-3.2 (1H, m), 3.2-3.3 (4H, m), 4.12 (2H, s), 4.19 (2H, q, J=7 Hz), 6.65 (2H, d, J=8 Hz), 7.63 (2H, d, J=8 Hz), 7.88 (2H, d, J=8 Hz), 8.00 (2H, d, J=8 Hz).

(7) N-[4-[3-[4-Isopropyl-2-[4-(trifluoromethyl)phenyl]thiazol-5-yl]propionyl]phenyl]-N-methylglycine The obtained ethyl ester of N-[4-[3-[4-isopropyl-2-[4-(trifluoromethyl)phenyl]thiazol-5-yl]propionyl]phenyl]-N-methylglycine (54 mg, 0.104 mmol) was dissolved in ethanol (1 mL) and THF (1 mL). 1N sodium hydroxide (208 μL, 0.208 mmol) was added to the solution. The mixture was stirred at room temperature for 20 minutes, diluted with water (2 mL), neutralized with 1N aqueous solution of hydrochloric acid, and stirred at 5° C. for 30 minutes. The precipitate was filtered, washed with water, and dried at 60° C. for 2 hours under reduced pressure to give the desired compound (40 mg) as yellow crystalline product (yield 78%).

FAB-MS (m/e): 491 (M+1)

$^1$H NMR(CDCl$_3$, 400 MHz): δ=1.32 (6H, d, J=7 Hz), 3.1-3.2 (4H, m), 3.2-3.3 (4H, m), 4.17 (2H, s), 6.66 (2H, d, J=8 Hz), 7.63 (2H, d, J=8 Hz), 7.89 (2H, d, J=8 Hz), 7.99 (2H, d, J=8 Hz).

Example 8

N-[4-[3-[4-Isopropyl-2-[4-(trifluoromethyl)phenyl]thiazol-5-yl]propionyl]phenyl]glycine (1) Ethyl ester of N-[4-[3-[4-Isopropyl-2-[4-(trifluoromethyl)phenyl]thiazol-5-yl]propionyl]phenyl]glycine The desired compound was obtained in an analogous manner to (6) of Example 7 from 1-(4-aminophenyl)-3-[4-isopropyl-2-[4-(trifluoromethyl)phenyl]thiazol-5-yl]-propan-1-one.

Pale Yellow Amorphous
Yield 83%

$^1$H NMR (CDCl$_3$, 400 MHz): δ=1.31 (3H, t, J=7 Hz), 1.33 (6H, d, J=7 Hz), 3.1-3.3 (5H, m), 3.95 (2H, d, J=5 Hz), 4.27 (2H, q, J=7 Hz), 4.82 (1H, m), 6.58 (2H, d, J=8 Hz), 7.63 (2H, d, J=8 Hz), 7.86 (2H, d, J=8 Hz), 8.00 (2H, d, J=8 Hz).

(2) N-[4-[3-[4-Isopropyl-2-[4-(trifluoromethyl)phenyl]thiazol-5-yl]propionyl]phenyl]glycine The desired compound was obtained in an analogous manner to (7) of Example 7 from ethyl ester of N-[4-[3-[4-Isopropyl-2-[4-(trifluoromethyl)phenyl]thiazol-5-yl]propionyl]phenyl]glycine.

Yellow Crystalline Product
Yield 75%

$^1$H NMR (CDCl$_3$, 400 MHz): δ=1.33 (6H, d, J=7 Hz), 2.17 (1H, s), 3.1-3.3 (5H, m), 4.06 (2H, s), 6.60 (2H, d, J=8 Hz), 7.63 (2H, d, J=8 Hz), 7.87 (2H, d, J=8 Hz), 7.99 (2H, d, J=8 Hz).

Example 9

N-[4-[3-[3-Isopropyl-5-[4-(trifluoromethyl)phenyl]thiophen-2-yl]propionyl]phenyl]-N-methylglycine (1) Ethyl ester of N-(4-acetophenyl)-N-methylglycine 4-Methylaminoacetophenone (277 mg, 1.86 mmol) and diisopropylethylamine (485 μL, 2.79 mmol) were dissolved in anhydrous DMF (10 mL). Ethyl bromoacetate (372 mg, 2.23 mmol) was added to the solution. The mixture was stirred at 110° C. for 16 hours under nitrogen atmosphere. The mixture was cooled to room temperature. Diisopropylethylamine (162 μL, 0.93 mmol) and ethyl bromoacetate (155 mg, 0.93 mmol) were added to the mixture. The resulting mixture was stirred at 110° C. for 16 hours. The mixture was cooled to room temperature, diluted with ethyl acetate, washed with water, saturated brine, and dried with anhydrous sodium sulfate. The solvent was removed under reduced pressure. The obtained residue was purified by silica gel column chromatography with hexane/chloroform (1:1, v/v) to give the desired compound (274 mg) as brown oil (yield 63%).

$^1$H NMR (CDCl$_3$, 400 MHz): δ=1.26 (3H, t, J=7 Hz), 2.51 (3H, s), 3.14 (3H, s), 4.12 (2H, s), 4.20 (2H, q, J=7 Hz), 6.65 (2H, d, J=8 Hz), 7.87 (2H, d, J=8 Hz).

(2) Ethyl ester of N-[4-[3-[3-isopropyl-5-[4-(trifluoromethyl)phenyl]thiophen-2-yl]propenoyl]phenyl]-N-methylglycine The obtained ethyl ester of N-(4-acetophenyl)-N-methylglycine (92 mg, 0.389 mmol) was dissolved in anhydrous THF (2 mL). Molecular sieve (3A powder, 200 mg) was added to the solution. The mixture was cooled to 5° C. 21 Wt. % ethanol solution of sodium ethoxide (145 μL, 0.389 mmol) was dropwise added to the mixture under nitrogen atmosphere. The resulting mixture was stirred at the same temperature for 10 minutes. A solution (10 mL) of 3-isopropyl-5-(4-trifluoromethylphenyl)thiophene-2-carboaldehyde (116 mg, 0.389 mmol) in anhydrous THF was added to the mixture. The resulting mixture was stirred at the same temperature for 30 minutes. The mixture was neutralized with 1N aqueous solution of hydrochloric acid, and diluted with chloroform. The insoluble matters were filtered, washed with 0.2 N aqueous solution of hydrochloric acid and saturated brine, and dried with anhydrous sodium sulfate. The solvent was removed under reduced pressure. The residue was purified by silica gel column chromatography with hexane/ethyl acetate (9:1, v/v) to give the desired compound (100 mg) as crude.

(3) Ethyl ester of N-[4-[3-[3-isopropyl-5-[4-(trifluoromethyl)phenyl]thiophen-2-yl]propionyl]phenyl]-N-methylglycine The obtained crude of ethyl ester of N-[4-[3-[3-isopropyl-5-[4-(trifluoromethyl)phenyl]thiophen-2-yl]propenoyl]phenyl]-N-methylglycine (100 mg) was dissolved in anhydrous tetrahydrofuran (5 mL) and methanol (4 mL). Methanol suspension (1 mL) of 10% palladium-active carbon (10 mg) was added to the solution. The mixture was stirred at room temperature for 2 hours under hydrogen atmosphere. Insoluble matters were filtered. The solvent was removed under reduced pressure. The residue was purified by silica gel column chromatography with hexane/ethyl acetate (9:1, v/v) to give the desired compound (37 mg) as colorless oil (yield through two steps 18%).

$^1$H NMR (CDCl$_3$, 400 MHz): δ=1.2-1.3 (9H, m), 3.0-3.1 (1H, m), 3.14 (3H, s), 3.2-3.3 (4H, m), 4.12 (2H, s), 4.19 (2H, q, J=7 Hz), 6.65 (2H, d, J=9 Hz), 7.20 (1H, s), 7.57 (2H, d, J=8 Hz), 7.64 (2H, d, J=8 Hz), 7.90 (2H, d, J=9 Hz).

(4) N-[4-[3-[3-Isopropyl-5-[4-(trifluoromethyl)phenyl]thiophene-2-yl]propionyl]phenyl]-N-methylglycine The obtained ethyl ester of N-[4-[3-[3-isopropyl-5-[4-(trifluoromethyl)phenyl]thiophen-2-yl]propionyl]phenyl]-N-methylglycine (37 mg, 0.071 mmol) was dissolved in ethanol (0.5 mL) and THF (0.5 mL). 1N sodium hydroxide (143 μL, 0.143 mmol) was added to the solution. The mixture was stirred at room temperature for 30 minutes, neutralized with 1N aqueous solution of hydrochloric acid, and stirred at 5° C. for 20 minutes. Precipitated crystalline was filtered, washed with water and cooled ethanol, and dried at 50° C. for 1 hour under reduced pressure to give the desired compound (26 mg) as white crystalline product (yield 75°).

FAB-MS (m/e): 490 (M+1)

$^1$H NMR (CDCl$_3$, 400 MHz): δ=1.25 (6H, d, J=7 Hz), 3.0-3.1 (1H, m), 3.14 (3H, s), 3.1-3.3 (4H, m), 4.18 (2H, s), 6.67 (2H, d, J=8 Hz), 7.19 (1H, s), 7.57 (2H, d, J=8 Hz), 7.63 (2H, d, J=8 Hz), 7.91 (2H, d, J=8 Hz).

Example 10

N-[4-[3-[2-(4-chloro-2-hydroxyphenyl)-5-isopropyl-4-oxazolyl]propionyl]phenyl]-N-methylglycine (1) Ethyl ester of N-[4-[3-[2-(4-chloro-2-hydroxyphenyl)-5-isopropyl-4-oxazolyl]propionyl]phenyl]-N-methylglycine The desired compound was obtained in an analogous manner to (2) of Example 9 from 2-(4-chloro-2-hydroxyphenyl)-5-isopropyloxazole-4-carboaldehyde and ethyl ester of N-(4-acetophenyl)-N-methylglycine.
Yellowish Brown Crystalline Product
Yield 49%
$^1$H NMR (CDCl$_3$, 400 MHz): δ=1.27 (3H, t, J=7 Hz), 1.39 (6H, d, J=7 Hz), 3.18 (3H, s), 3.3-3.5 (1H, m), 4.16 (2H, s), 4.22 (2H, q, J=7 Hz), 6.71 (2H, d, J=9 Hz), 6.97 (1H, dd, J=2 Hz, 8 Hz), 7.13 (1H, d, J=2 Hz), 7.66 (1H, d, J=15 Hz), 7.71 (1H, d, J=15 Hz), 7.76 (1H, d, J=8 Hz), 8.03 (2H, d, J=9 Hz), 11.38 (1H, s).

(2) Ethyl ester of N-[4-[3-[2-(4-chloro-2-hydroxyphenyl)-5-isopropyl-4-oxazolyl]propionyl]phenyl]-N-methylglycine The desired compound was obtained in an analogous manner to (3) of Example 9 from the obtained ethyl ester of N-[4-[3-[2-(4-chloro-2-hydroxyphenyl)-5-isopropyl-4-oxazolyl]propionyl]phenyl]-N-methylglycine.
Slightly Yellow Crystalline Product
Yield 53%
$^1$H NMR (CDCl$_3$, 400 MHz): δ=1.25 (3H, t, J=7 Hz), 1.31 (6H, d, J=7 Hz), 2.93 (2H, t, J=7 Hz), 3.13 (3H, s), 3.1-3.3 (1H, m), 3.25 (2H, t, J=7 Hz), 4.11 (2H, s), 4.19 (2H, q, J=7 Hz), 6.64 (2H, d, J=9 Hz), 6.90 (1H, dd, J=1 Hz, 8 Hz), 7.05 (1H, d, J=1 Hz), 7.68 (1H, d, J=8 Hz), 7.88 (2H, d, J=9 Hz), 11.53 (1H, s).

(3) N-[4-[3-[2-(4-chloro-2-hydroxyphenyl)-5-isopropyl-4-oxazolyl]propionyl]phenyl]-N-methylglycine The desired compound was obtained in an analogous manner to (4) of Example 9 from the obtained ethyl ester of N-[4-[3-[2-(4-chloro-2-hydroxyphenyl)-5-isopropyl-4-oxazolyl]propionyl]phenyl]-N-methylglycine.
Pale Yellow Crystalline Product
Yield 85%
Melting point 166-168° C.
FAB-MS (m/e): 457 (M+1)
$^1$H NMR (CDCl$_3$, 400 MHz): δ=1.31 (6H, d, J=7 Hz), 2.93 (2H, t, J=7 Hz), 3.14 (3H, s), 3.1-3.3 (1H, m), 3.26 (2H, t, J=7 Hz), 4.18 (2H, s), 6.66 (2H, d, J=9 Hz), 6.90 (1H, dd, J=2 Hz, 9 Hz), 7.04 (1H, d, J=2 Hz), 7.68 (1H, d, J=9 Hz), 7.89 (2H, d, J=9 Hz).

Example 11

3-[4-[3-[4-Isopropyl-2-[4-(trifluoromethyl)phenyl]-5-thiazolyl]propionyl]-2-ethylphenyl]propionic acid (1) Methyl 3-[2-ethyl-4-[3-[4-isopropyl-2-[4-(trifluoromethyl)phenyl]-5-thiazolyl]propenoyl]phenyl] acrylate The desired compound was obtained in an analogous manner to (5) of Example 1 from 4-isopropyl-2-[4-(trifluoromethyl)phenyl]thiazole-5-carboaldehyde and methyl 3-(4-acetyl-2-ethylphenyl)acrylate.

Yellow Crystalline Product

Yield 55% (2 steps)

$^1$H NMR (CDCl$_3$, 400 MHz): δ=1.29 (3H, t, J=8 Hz), 1.39 (6H, d, J=7 Hz), 2.88 (2H, q, J=8 Hz), 3.4-3.5 (1H, m), 3.84 (3H, s), 6.47 (1H, d, J=15 Hz), 7.28 (1H, d, J=15 Hz), 7.7-7.8 (3H, m), 7.8-7.9 (2H, m), 8.0-8.2 (4H, m).

(2) Methyl 3-[2-ethyl-4-[3-[4-isopropyl-2-[4-(trifluoromethyl)phenyl]-5-thiazolyl]propionyl]phenyl]propionate The desired compound was obtained in an analogous manner to (6) of Example 1 from the obtained methyl 3-[2-ethyl-4-[3-[4-isopropyl-2-[4-(trifluoromethyl)phenyl]-5-thiazolyl]propenoyl]phenyl]acrylate.

Yellow Oil

Yield 60%

$^1$H NMR (CDCl$_3$, 400 MHz): δ=1.26 (3H, t, J=8 Hz), 1.34 (6H, d, J=7 Hz), 2.61 (2H, t, J=8 Hz), 2.72 (2H, q, J=8 Hz), 3.02 (2H, t, J=8 Hz), 3.1-3.2 (1H, m), 3.2-3.4 (4H, m), 3.68 (3H, s), 7.24 (1H, d, J=8 Hz), 7.64 (2H, d, J=8 Hz), 7.73 (1H, dd, J=2 Hz, 8 Hz), 7.80 (1H, d, J=2 Hz), 8.00 (2H, d, J=8 Hz).

(3) 3-[4-[3-[4-Isopropyl-2-[4-(trifluoromethyl)phenyl]-5-thiazolyl]propionyl]-2-ethylphenyl]propionic acid The desired compound was obtained in an analogous manner to (7) of Example 1 from the obtained methyl 3-[2-ethyl-4-[3-[4-isopropyl-2-[4-(trifluoromethyl)phenyl]-5-thiazolyl]propionyl]phenyl]propionate.

Pale Yellow Crystalline Product

Yield 74%

FAB-MS (m/e): 504 (M+1)

$^1$H NMR (CDCl$_3$, 400 MHz): δ=1.26 (3H, t, J=7 Hz), 1.33 (6H, d, J=7 Hz), 2.6-2.8 (4H, m), 3.03 (2H, t, J=8 Hz), 3.1-3.2 (1H, m), 3.2-3.4 (4H, m), 7.26 (1H, d, 8 Hz), 7.64 (2H, d, J=8 Hz), 7.74 (1H, dd, J=8 Hz, 2 Hz), 7.80 (1H, d, J=2 Hz), 8.00 (2H, d, J=8 Hz).

Example 12

3-[4-[3-[2-(4-Chloro-2-hydroxyphenyl)-5-isopropyl-4-oxazolyl]propionyl]-2-methylphenyl]propionic acid (1) Methyl 3-[4-[3-[2-(4-chloro-2-hydroxyphenyl)-5-isopropyl-4-oxazolyl]propenoyl]-2-methylphenyl]acrylate The desired compound was obtained in an analogous manner to (5) of Example 1 from 2-(4-chloro-2-hydroxyphenyl)-5-isopropyloxazole-4-carboaldehyde and methyl 3-(4-acetyl-2-ethylphenyl)acrylate.

Pale Brown Crystalline Product

Yield 61%

$^1$H NMR (CDCl$_3$, 400 MHz): δ=1.41 (6H, d, J=7 Hz), 2.54 (3H, s), 3.3-3.5 (1H, m), 3.84 (3H, s), 6.47 (1H, d, J=16 Hz), 6.98 (1H, dd, J=2 Hz, 9 Hz), 7.13 (1H, d, J=2 Hz), 7.64 (1H, d, J=15 Hz), 7.67 (1H, d, J=9 Hz), 7.73 (1H, dc, J=15 Hz), 7.77 (1H, d, J=8 Hz), 7.8-7.9 (2H, m), 7.99 (1H, d, J=16 Hz), 11.27 (1H, s).

(2) Methyl 3-[4-[3-[2-(4-chloro-2-hydroxyphenyl)-5-isopropyl-4-oxazolyl]propionyl]-2-methylphenyl]propionate The desired compound was obtained in an analogous manner to (6) of Example 1 from the obtained methyl 3-[4-[3-[2-(4-chloro-2-hydroxyphenyl)-5-isopropyl-4-oxazolyl]propenoyl]-2-methylphenyl]acrylate.

Colorless Oil

Yield 47%

$^1$H NMR (CDCl$_3$, 40 MHz): δ=1.32 (6H, d, J=7 Hz), 2.36 (3H, s), 2.59 (2H, t, J=8 Hz), 2.94 (2H, t, J=7 Hz), 2.98 (2H, t, J=8 Hz), 3.1-3.3 (1H, m), 3.33 (2H, t, J=7 Hz), 3.68 (3H, s), 6.90 (1H, dd, J=2 Hz, 8 Hz), 7.04 (1H, d, J=2 Hz), 7.21 (1H, d, J=8 Hz), 7.68 (1H, d, J=8 Hz), 7.7-7.8 (2H, m), 11.47 (1H, s).

(3) 3-[4-[3-[2-(4-Chloro-2-hydroxyphenyl)-5-isopropyl-4-oxazolyl]propionyl]-2-methylphenyl]propionic acid The desired compound was obtained in an analogous manner to (7) of Example 1 from the obtained methyl 3-[4-[3-[2-(4-chloro-2-hydroxyphenyl)-5-isopropyl-4-oxazolyl]propionyl]-2-methylphenyl]propionate.

White Crystalline Product

Yield 93%

Melting point 141-144° C.

FAB-MS (m/e): 456 (M+1)

$^1$H NMR (CDCl$_3$, 400 MHz): δ=1.32 (6H, d, J=7 Hz), 2.37 (3H, s), 2.65 (2H, t, J=8 Hz), 2.95 (2H, t, J=7 Hz), 2.99 (2H, t, J=8 Hz), 3.1-3.3 (1H, m), 3.33 (2H, t, J=7 Hz), 6.90 (1H, dd, J=2 Hz, 8 Hz), 7.04 (1H, d, J=2 Hz), 7.24 (1H, d, J=8 Hz), 7.68 (1H, d, J=8 Hz), 7.7-7.8 (2H, m).

Example 13

3-[4-[3-[5-Isopropyl-2-(2-hydroxyphenyl)-4-oxazolyl]propionyl]-2-methylphenyl]propionic acid (1) Methyl 3-[4-[3-[5-isopropyl-2-(2-hydroxyphenyl)-4-oxazolyl]propionyl]-2-methylphenyl]propionate Methyl 3-[4-[3-[5-isopropyl-2-(2-methoxyphenyl)-4-oxazolyl]propionyl]-2-methylphenyl]propionate (24 mg, 0.0534 mmol) was dissolved in methylene chloride (1.2 mL) 1M dichloromethane solution of trichloroborane (127 μL, 0.127 mmol) was added to the solution at 0° C. The mixture was stirred at room temperature for 24 hours. Ice-cold water (5 mL) was added to the mixture. The resulting mixture was extracted with chloroform. The organic layer was washed with saturated aqueous solution of sodium carbonate and water, and dried with anhydrous sodium sulfate. The solvent was removed under reduced pressure. The obtained residue was purified by silica gel column chromatography with hexane/ethyl acetate (3:1, v/v) to give the desired compound (4 mg) as white crystalline product (yield 17%).

White Crystalline Product

Yield 17%

$^1$H NMR (CDCl$_3$, 400 MHz): δ=1.32 (6H, d, J=7 Hz), 2.36 (3H, s), 2.59 (2H, t, J=7 Hz), 2.9-3.0 (4H, m), 3.1-3.3 (1H, m), 3.34 (2H, t, J=7 Hz), 3.68 (3H, s), 6.92 (1H, t, J=8 Hz), 7.03 (1H, d, J=8 Hz), 7.21 (1H, d, J=8 Hz), 7.2-7.3 (1H, m), 7.7-7.8 (3H, m).

(2) 3-[4-[3-[5-Isopropyl-2-(2-hydroxyphenyl)-4-oxazolyl]propionyl]-2-methylphenyl]propionic acid The desired compound was obtained in an analogous manner to (7) of Example 1 from the obtained methyl 3-[4-[3-[5-isopropyl-2-(2-hydroxyphenyl)-4-oxazolyl]propionyl]-2-methylphenyl]propionate.

White Powder
Yield 75%
FAB-MS (m/e): 422 (M+1)
$^1$H NMR (CDCl$_3$, 400 MHz): δ=1.32 (6H, d, J=7 Hz), 2.37 (3H, s), 2.65 (2H, t, J=7 Hz), 2.9-3.0 (4H, m), 3.1-3.3 (1H, m), 3.34 (2H, t, J=7 Hz), 6.92 (1H, t, J=8 Hz), 7.02 (1H, d, J=8 Hz), 7.2-7.3 (2H, m), 7.7-7.8 (3H, m).

Example 14

Pharmacological Tests 1

I. Method of Measurement

PPAR activating functions of test compounds (compounds of Examples) were measured in the manner described below.

A receptor expression plasmid (pSG5-GAL4-hPPARα or γ or δ (LBD)), a luciferase expression plasmid (pUC8-MH100×4-TK-Luc), and a β-galactosidase expression plasmid (pCMX-β-GAL) were transfected into CV-1 cells (ATCC) (Kliewer, S. A. et al., (1992) Nature, 358: 771-774). After the gene transfer was conducted by utilizing a lipofection reagent (Lipofectamine 2000, Invitrogen), it was incubated for about 40 hours in the presence of a compound to be tested. The luciferase activity and β-GAL activity were measured on the soluble cells.

The luciferase activity was calibrated by the β-GAL activity. A relative ligand activity was calculated under the condition that the luciferase activity of the cells treated by GW-590735 for PPARα, Rosiglitazone for PPARδ, or GW-501516 for PPARδ was set to 100% to determine EC$_{50}$.

II. Results
The results of tests are shown in Table 38.

TABLE 38

| Test compounds | PPAR activity | | |
|---|---|---|---|
| | PPARα | PPARγ | PPARδ |
| Example 1 | Inactive | Inactive | 56 |
| Example 2 | Inactive | Inactive | 88 |
| Example 3 | Inactive | Inactive | 76 |
| Example 4 | Inactive | Inactive | 22 |
| Example 5 | Inactive | Inactive | 114 |
| Example 6 | Inactive | Inactive | 68 |
| Example 7 | Inactive | Inactive | 81 |

TABLE 38-continued

| Test compounds | PPAR activity | | |
|---|---|---|---|
| | PPARα | PPARγ | PPARδ |
| Example 8 | Inactive | Inactive | 61 |
| Example 9 | Inactive | Inactive | 80 |

PPAR activity: a relative value using 10$^{-7}$M of the test compound (control = 100%)
α: GW-590735 10$^{-6}$ M
γ: Rosiglitazone 10$^{-5}$ M
δ: GW-501516 10$^{-7}$ M
(Except that compounds of Examples 3 and 8 were measured in the amount of 10$^{-6}$ M)

As is apparent from Table 38, the test compound show excellent agonist functions for PPARδ. The compound of Example 5 shows the particularly strong agonist function for PPARδ.

Example 15

Pharmacological Tests 2

The tests were conducted in the same manner to Example 14 (1).

The results of tests are shown in Table 39.

TABLE 39

| Test compounds | PPAR activity | | |
|---|---|---|---|
| | PPARα | PPARγ | PPARδ |
| Example 10 | Inactive | Inactive | 69 |
| Example 11 | Inactive | Inactive | 89 |
| Example 12 | Inactive | Inactive | 93 |
| Example 13 | Inactive | Inactive | 62 |

PPAR activity: a relative value using 10$^{-7}$M of the test compound (control = 100%)
α: GW-590735 10$^{-6}$ M
γ: Rosiglitazone 10$^{-5}$ M
δ: GW-501516 10$^{-7}$ M
(Except that compound of Example 13 was measured in the amount of 10$^{-6}$ M)

As is apparent from Table 39, the test compound show excellent agonist functions for PPARδ.

The invention claimed is:
1. A compound selected from the group consisting of:
N-[4-[3-[4-Isopropyl-2-[4-(trifluoromethyl)phenyl]thiazol-5-yl]propionyl]phenyl]-N-methylglycine; and
N-[4-[3-[2-(4-chloro-2-hydroxyphenyl)-5-isopropyl-4-oxazolyl]propionyl]phenyl]-N-methylglycine;
or a pharmaceutically acceptable salt thereof.
2. A medicament which contains the compound of claim 1 or salt thereof and a pharmaceutically acceptable vehicle.
3. A method for treatment of a disease mediated by peroxisome proliferator activated receptor delta comprising administering to a patient in need thereof an effective dose of a compound of claim 1, wherein the disease is dyslipidemia, metabolic syndrome, obesity, atherosclerosis, or diabetes.

* * * * *